US009641799B2

(12) United States Patent
Smurro

(10) Patent No.: US 9,641,799 B2
(45) Date of Patent: *May 2, 2017

(54) MULTIMODAL COGNITIVE COMMUNICATIONS AND COLLABORATIVE KNOWLEDGE EXCHANGE WITH VISUAL NEURAL NETWORKING AND PACKETIZED AUGMENTED INTELLIGENCE

(71) Applicant: James Paul Smurro, San Clemente, CA (US)

(72) Inventor: James Paul Smurro, San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/544,807

(22) Filed: Feb. 18, 2015

(65) Prior Publication Data
US 2016/0119582 A1    Apr. 28, 2016

Related U.S. Application Data

(63) Continuation-in-part of application No. 13/999,688, filed on Mar. 15, 2014.
(Continued)

(51) Int. Cl.
*H04N 7/14* (2006.01)
*H04N 7/15* (2006.01)
(Continued)

(52) U.S. Cl.
CPC ........... *H04N 7/15* (2013.01); *G06F 19/3425* (2013.01); *G06Q 10/101* (2013.01); *G06Q 50/22* (2013.01);
(Continued)

(58) Field of Classification Search
None
See application file for complete search history.

(56) References Cited

U.S. PATENT DOCUMENTS

2007/0118389 A1* 5/2007 Shipon ................ G06F 19/3418
379/203.01
2013/0173305 A1* 7/2013 Hyde .................. G06F 19/3481
705/3

* cited by examiner

*Primary Examiner* — Maria El-Zoobi

(57) ABSTRACT

The invention enables multimodal cognitive communications, collaboration, consultation and instruction with multichannel multiplexed streaming imagery data. It also enables synchronous multiparty curation, multisensory annotation and metadata tagging, as well as multi-formatted encapsulation, saving and sharing of collaborated imagery data as packetized augmented intelligence. The invention acquires both live stream and archived medical modality imagery from network-connected medical devices, cameras, signals and sensors, as well as multi-omic [phenotypic, genomic, metabolomic and radiomic] clinical data from biometric maps and movies, hapmaps, heat maps and data stream visualizations. The invention also acquires both medical and non-medical streaming imagery data from image data repositories, documents and structured reports, workstations and mobile devices, as well as from wearable computing, signals and sensors. The invention enables networked teams to interactively communicate, concurrently collaborate and bi-directionally exchange multichannel multiplexed imagery data streams, singly or together, in real time or asynchronously, generally by curating, annotating and tagging imagery information objects. The invention encapsulates and saves collaborated imagery data, together with multisensory annotations and metadata tags, in standard file formats as packetized augmented intelligence. The invention enables recursive cognitive enrichment with augmented cognitive vismemes, and saves packetized imagery information objects, multisensory annotations and metadata tags in native file formats [PDF, MPEG, JPEG, XML, XMPP, OR, SVG and DAE[ as well as in formats compliant with standards for digital communications in medicine [DI- (Continued)

COM]. The invention enables live stream multicasting of multimodal cognitive communications and collaborative knowledge exchange with multisensory [visual, auditory, haptic] annotation and tagging of streaming imagery data, as well as secure, encrypted transmission of packetized augmented intelligence across file sharing data networks for rapid, adaptive learning, specialist skills acquisition and interoperable health information exchange.

13 Claims, 23 Drawing Sheets

Related U.S. Application Data

(60) Provisional application No. 61/967,323, filed on Mar. 15, 2014, provisional application No. 61/852,625, filed on Mar. 15, 2013.

(51) Int. Cl.
*G06Q 10/10* (2012.01)
*G06Q 50/22* (2012.01)
*H04L 29/06* (2006.01)
*H04L 12/18* (2006.01)
*H04M 3/56* (2006.01)
*G06F 19/00* (2011.01)

(52) U.S. Cl.
CPC ...... *H04L 12/1813* (2013.01); *H04L 12/1822* (2013.01); *H04L 65/1089* (2013.01); *H04L 65/403* (2013.01); *H04L 65/4015* (2013.01); *H04M 3/567* (2013.01); *G06F 19/321* (2013.01)

FIG. 9

TIMS Clini-Pod deployment as Hub-n-Spoke Device Cluster for either Server-Based or Peer-to-Peer Networks TIMS 4-Party Team CNS Network Server Interconnecting with four TIMS Clini-Pods TIMS 4-Party Hive CNS Network Server Interconnecting with four TIMS Team CNS Network Servers Alternative Network Architectures for TIMS Clini-Pod Deployment:
Point-to-Point vs Hub-and-Spoke vs Chord

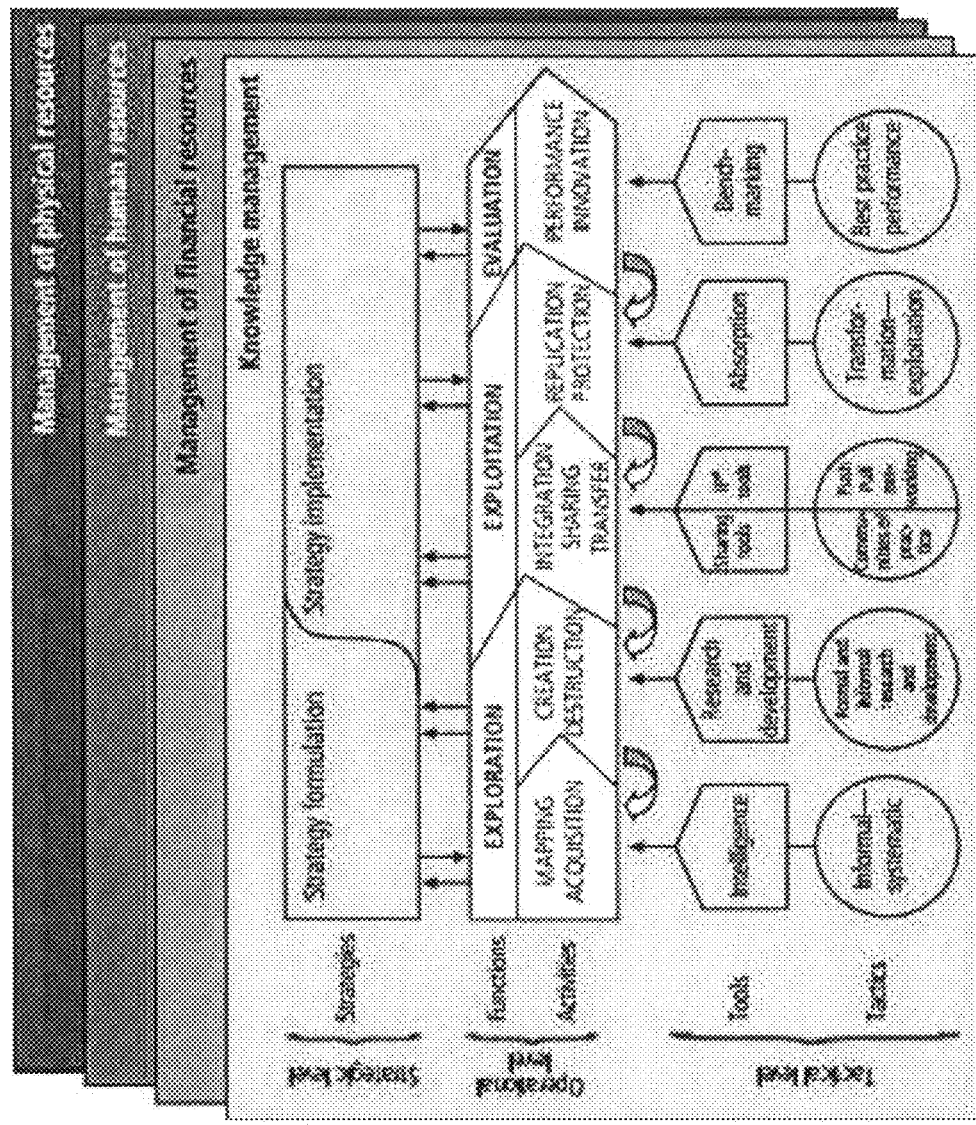
FIG 17. Value Chain Knowledge Exchange

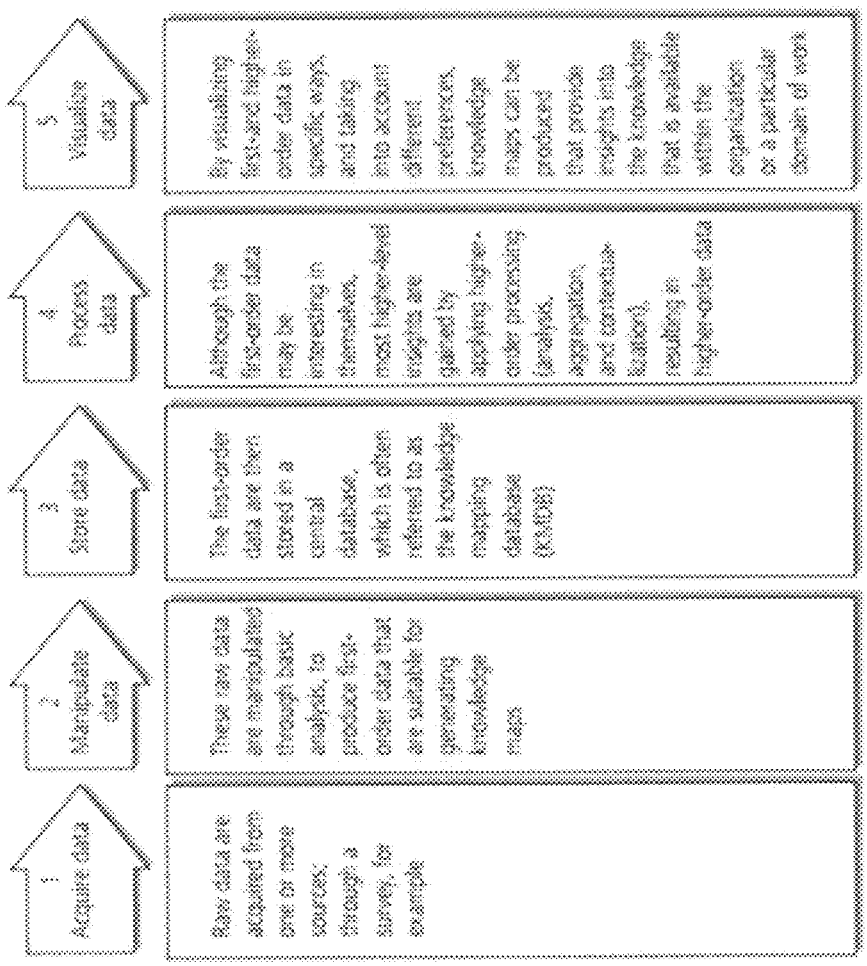
FIG. 18. Interactive Data Visualization Processes

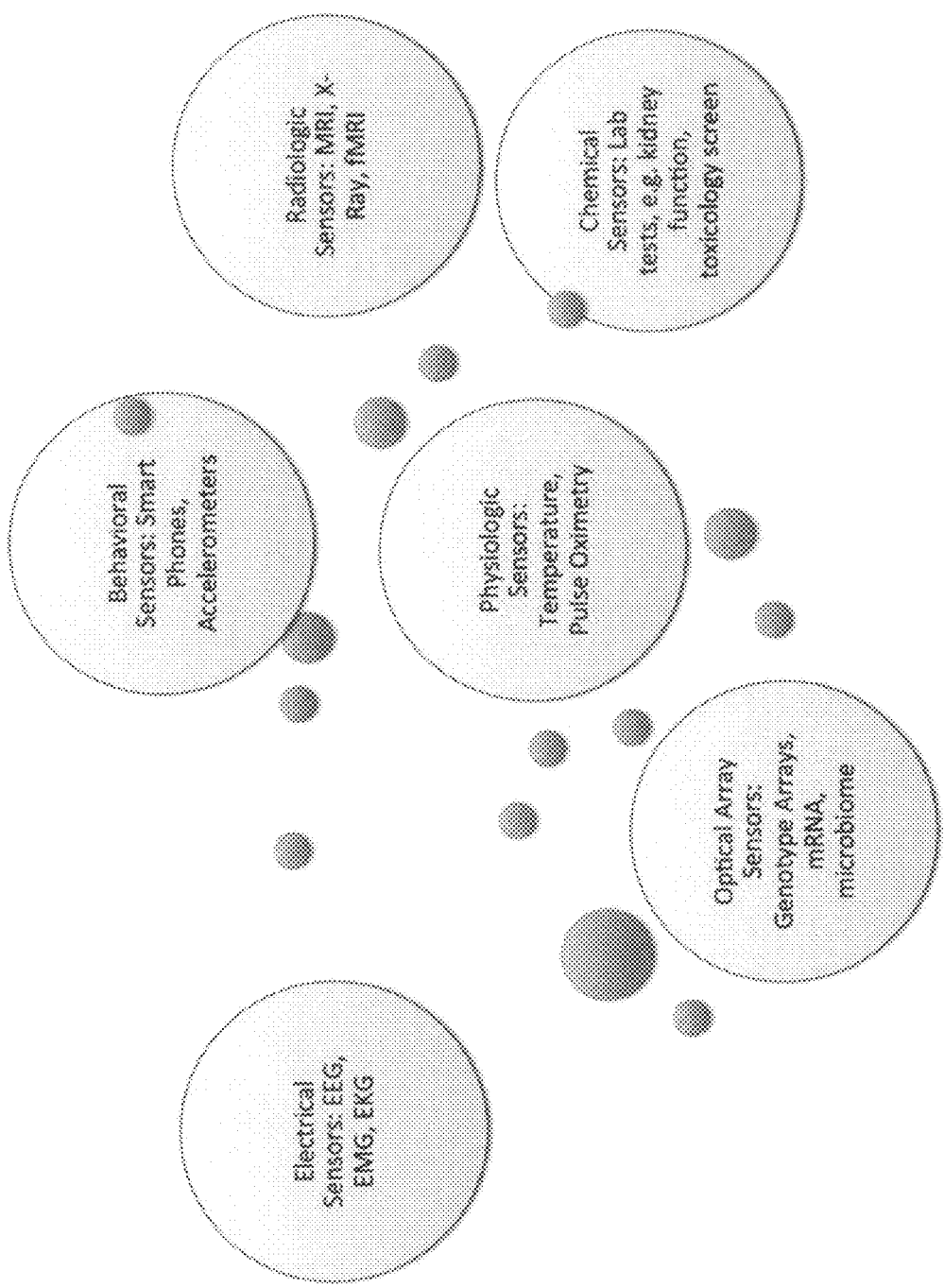
FIG 19. Interactive Data Visualization Sensors

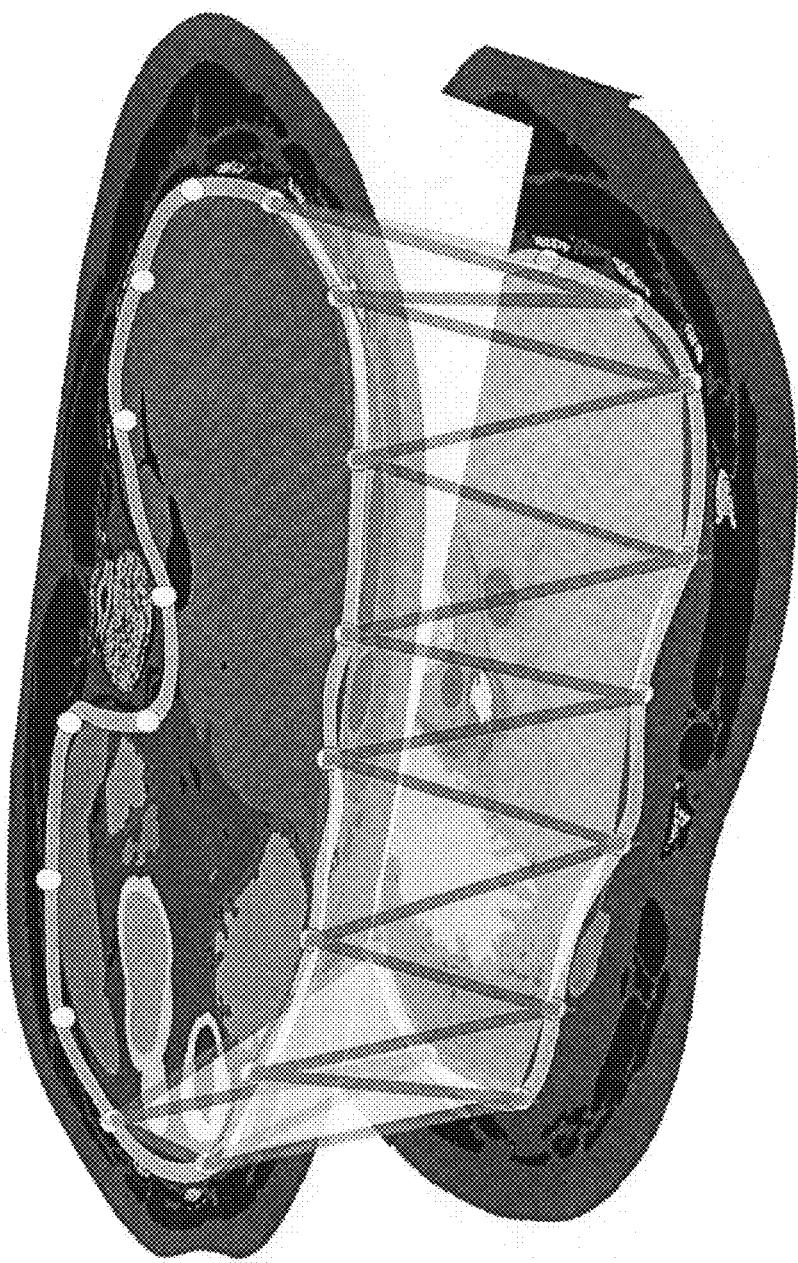
FIG 20. Interactive Data Visualization Slices

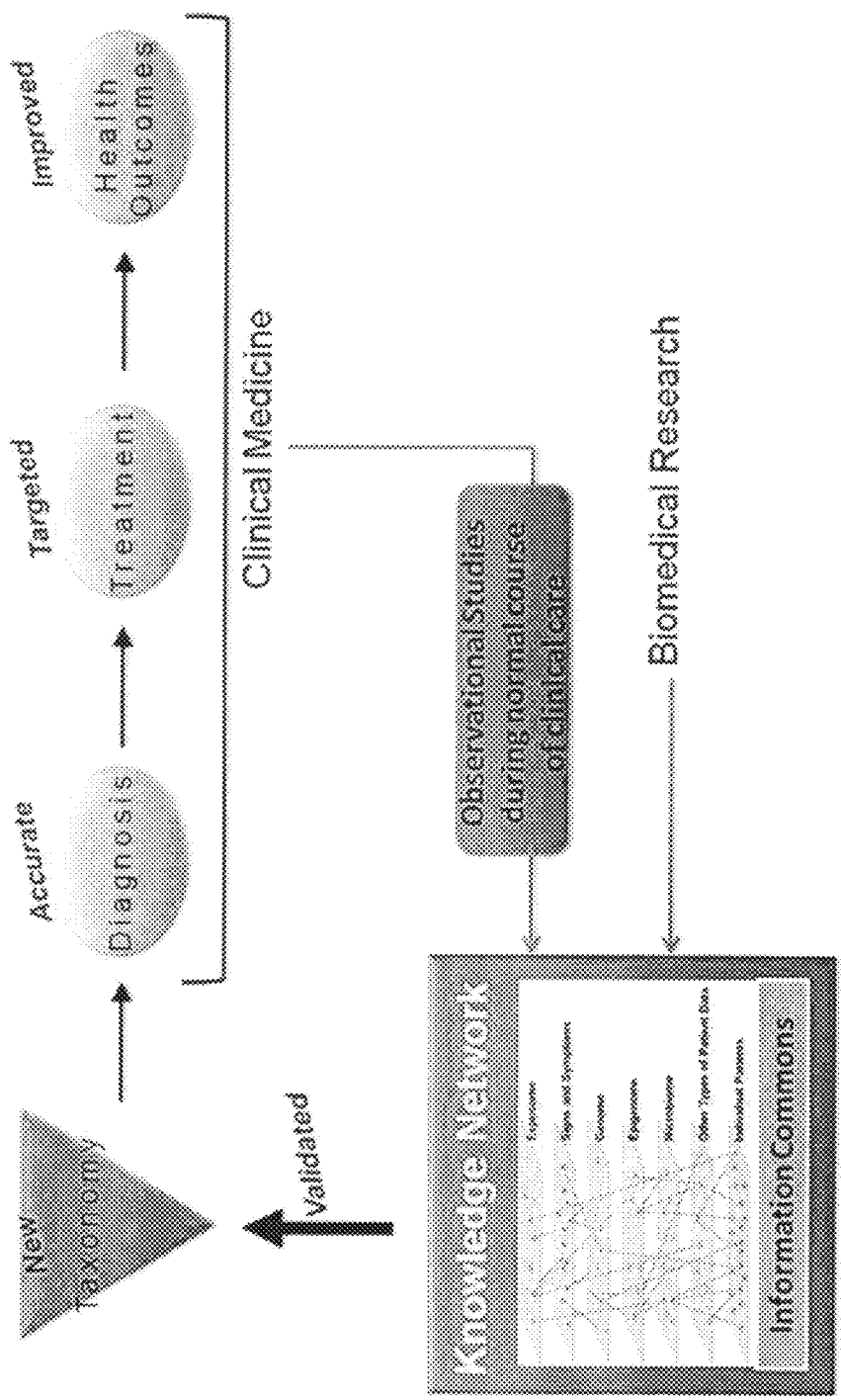
FIG 21. Knowledge Networks for Biomedical Research

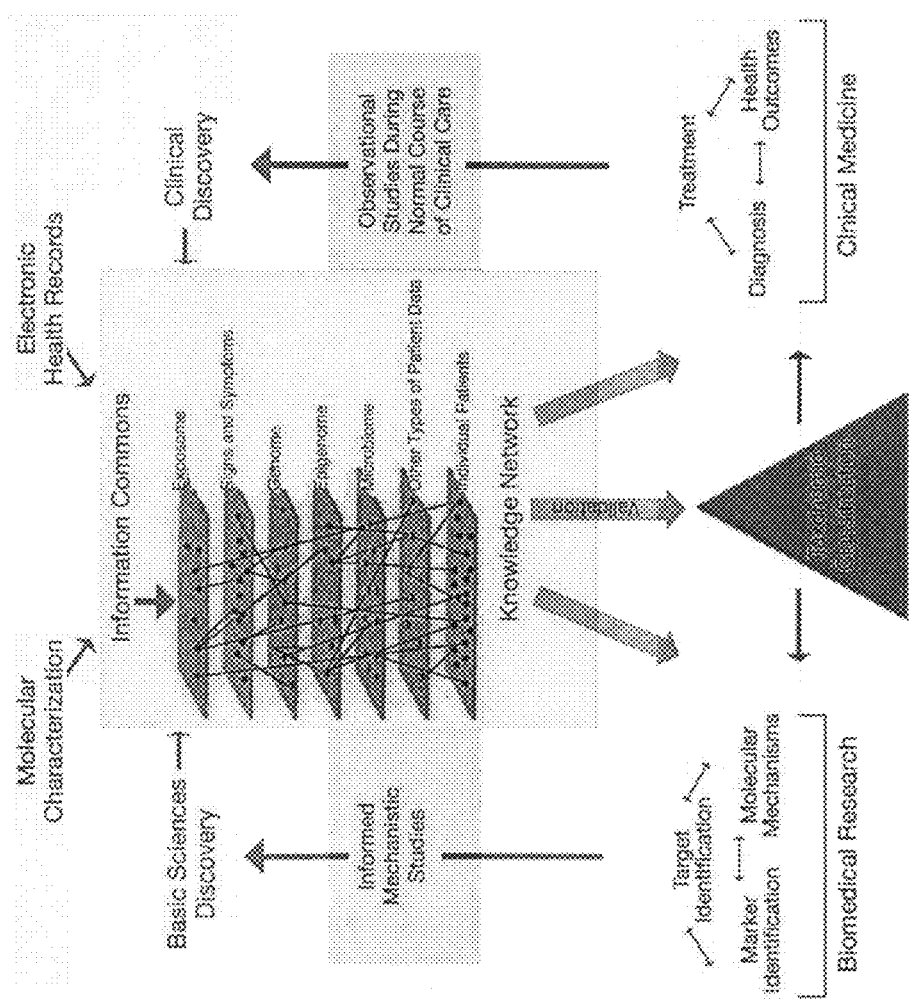
FIG 22. Knowledge Networks for Precision Medicine

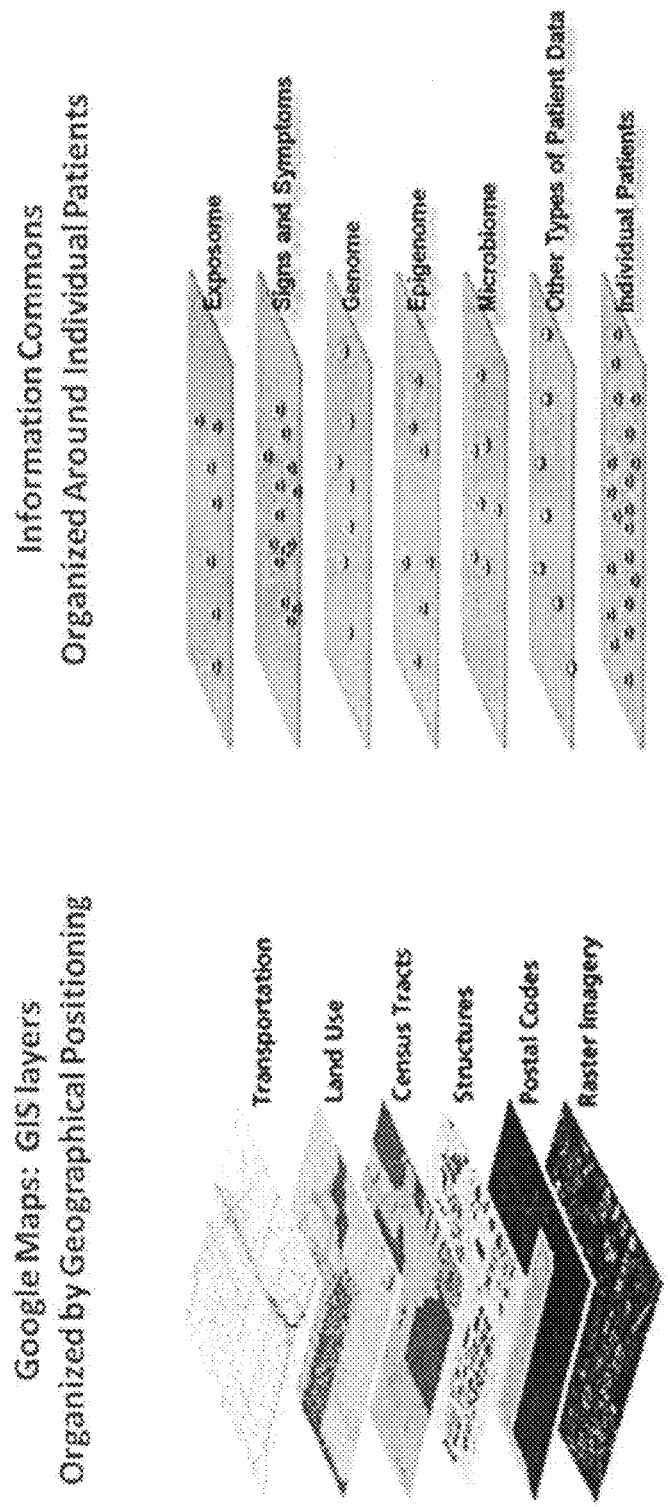
FIG. 23. Patient-Centric Precision Medicine

MULTIMODAL COGNITIVE COMMUNICATIONS AND COLLABORATIVE KNOWLEDGE EXCHANGE WITH VISUAL NEURAL NETWORKING AND PACKETIZED AUGMENTED INTELLIGENCE

CROSS-REFERENCE TO RELATED APPLICATIONS

This application claims the benefit of U.S. Provisional Application No. 61/967,323 filed Mar. 15, 2014 entitled:
"Network systems apparatus and method of use adapted for tele-visual communications and collaboration with streaming medical imagery and clinical informatics by networked teams of minds, machines, languages and tools, including recursively annotating, tagging, encapsulating and saving shared tele-visual communications, collaborations, imagery and informatics together as clinical cognitive vismemes in standard known file formats for interoperable delivery of personalized medicine"
naming as inventor James Smurro, which is incorporated herein by reference in its entirety.

This application claims the benefit of U.S. Ser. No. 13/999,688 filed Mar. 15, 2014 entitled:
"Network system apparatus and method of use adapted for visual neural networking with multi-channel multiplexed streaming medical imagery and packetized clinical informatics"
naming as inventor James Smurro, which is incorporated herein by reference in its entirety.

This application may be related to the following commonly assigned and commonly filed U.S. patent applications, each of which is incorporated herein by reference in its entirety:
1. U.S. Pat. No. 8,924,864 B2 entitled "System and method for collaboratively communicating on images and saving those communications and images in a standard known format", naming as inventors Mariotti et al, issued 30 Dec. 2014.
2. U.S. patent application 20140176661 A1 entitled "System and method for surgical telementoring and training with virtualized telestration and haptic holograms, including metadata tagging, encapsulation and saving multi-modal streaming medical imagery together with multi-dimensional [4-d] virtual mesh and multi-sensory annotation in standard file formats used for digital imaging and communications in medicine (dicom)", naming as inventors Smurro et al, published 26 Jun. 2014.
3. U.S. Pat. No. 7,925,980 B2 entitled "N-way multimedia collaboration systems", naming as inventors Bakir et al., issued 12 Apr. 2011.
4. U.S. patent application Ser. No. US 20050251009 A1 entitled "System and method for storing and retrieving a communication session", naming as inventors Morita et al., published 10 Nov. 2005.
5. U.S. patent application Ser. No. U.S. Pat. No. 6,424,996 B1 entitled "Medical network system and method for transfer of information", naming as inventors Killcommons et al., issued 23 Jul. 2002.
6. U.S. patent application Ser. No. U.S. Pat. No. 7,257,832 B2 entitled "Medical image capture system and method", naming as inventors Beane et al., issued 14 Aug. 2007.

STATEMENT REGARDING NON PATENT LITERATURE DOCUMENTS

1. Realizing the Full Potential of Health Information Technology to Improve Healthcare for Americans: The Path Forward—President's Council of Advisors on Science and Technology (PCAST) [December 2010]
2. US Office of National Coordinator Standards and Interoperability (S&I) Framework:
    a. Standards and Interoperability (S&I) Initiative
    b. ONC Resource Supports Consolidated CDA Standards Implementation
    c. S&I Structured Data Capture Implementation Guide
    d. S&I Clinical Element Data Dictionary [CEDD] Reference Materials
3. LAND and SEE architecture—MeHI Massachusetts eHealth Institute
4. DICOM Standard—the 2013 Interim Edition Issued for Public Review—MITA Medical Imaging and Technology Alliance [Feb. 28, 2013]
5. Telecommunications Management Network (TMN) Architecture—International Engineering Consortium (IEC)
6. Toward Precision Medicine: Building a Knowledge Network for Biomedical Research and a New Taxonomy of Disease [National Research Council (US) Committee on A Framework for Developing a New Taxonomy of Disease. [Nov. 2, 2011]
7. Digital Imaging and Communications in Medicine (DICOM) Sup 172—Parametric Map Storage—Working Group 18—Research and Clinical Trials [Nov. 11, 2014]
8. The knowledge-value chain: A conceptual framework for knowledge translation in health. Bull World Health Organ. 2006 August; 84(8): 597-602.
9. Knowledge mapping as a technique to support knowledge translation. Bull World Health Organ. 2006 August; 84(8): 636-642.

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISC APPENDIX

Not applicable

FIELD

The invention relates generally to a medical apparatus and method of using the same for receiving and transmitting streaming imagery data, including medical images, waveforms, audio and haptic signals, biomedical and clinical documents, both live and asynchronously, allowing operators to concurrently annotate, telestrate, to encapsulate and save that imagery data, together with those annotations and including searchable metadata tags in single file formats. The invention acquires streaming imagery data through an input device, and enables a variety of clinical collaborants, singly or together, to electronically concurrently collaborate, generally by telestrating, annotating, sketching image overlays on a streaming imagery data, and saving those images together with annotations and metadata, as collaborated imagery files [also known as CIF's] in acceptable file formats for interoperable health information exchange across file sharing data networks.

The invention enables pluribus network encoding with multichannel multiplexed signals, sensors, devices, packets, waveforms and streams, including space shifting, time shifting and format shifting media synchronization. The invention enables networked teams to recursively annotate and tag, encapsulate and share multichannel multiplexed imagery data streams, including interactive data visualization and bi-directional knowledge exchange, with streaming imagery data from heterogeneous spatial and temporal sources, locations, modalities and scales. The invention acquires both live stream and archived medical imagery data from network-connected medical devices, cameras, signals and sensors. The network system apparatus also acquires phenotypic and genomic data from biometric maps, movies, data visualizations, hapmaps and heat maps. The network system apparatus also acquires packetized clinical informatics from imagery data repositories, from clinical workstations and mobile medical devices, as well as from wearable computing devices, signals and sensors.

The invention enables networked teams to interactively communicate, concurrently collaborate and bi-directionally exchange multichannel multiplexed imagery data streams, singly or together, in real time or asynchronously, generally by annotating and tagging imagery information objects. The invention encapsulates and saves collaborated imagery data streams, together with collaborated clinical annotations and personal health identifying [PHI] privacy protected metadata, in standard known file formats as medical dicom vismemes—encapsulated packets, waveforms and streams. Medical dicom vismemes preserve packetized imagery information objects, clinical annotations and metadata tags in native file format structures, including PDF, MPEG, JPEG, XML, QR, SVG and DAE, as well as DICOM.

Medical dicom vismemes allow for networked cognitive enrichment through recursive annotation, tagging, encapsulation and saving, together with value chain knowledge exchange. Value chain knowledge exchange includes knowledge acquisition and mapping, creation and destruction, integration and sharing, replication and protection, as well as performance evaluation and innovation.

The invention also provides for networked collaborative innovation and value chain knowledge exchange with multisensory cognitive communications and interactive data visualization. Multisensory cognitive communications includes multisensory [sight-sound-touch] digital data exchange with vision, audition and sensation [semiotics, semantics, somesthetics.]

The invention enables live stream multicasting of N-way multi-party collaborations, including interactive data visualization and bi-directional knowledge exchange, with multichannel multiplexed imagery data streams, and concurrent transmission of secure, encrypted medical dicom vismemes across collaborative file sharing networks for interoperable health information exchange.

BACKGROUND

This invention relates to a videoconferencing system for 'live', e.g., real time, near real time or minimally latent, viewing of streaming medical imagery, and more particularly, to a network systems apparatus and method of using said medical imaging videoconferencing system with multiple input operators or participant clients viewing each other's inputs collaboratively and concurrently.

Videoconferencing systems are becoming more commonly used to conduct meetings and share information, including in the medical field. Participants are typically geographically separated and wish to share ideas and thoughts as they participate in the conference. With such a videoconferencing system, audio and video signals are transmitted over a communication link, such as telephonic, to be reproduced at a remote videoconferencing system so the parties can see and hear each other. In many cases, the videoconferencing systems can support video images allowing each party to view moving camera images, as well as other screen displays. Videoconferencing systems are used in many different ways. Some of the most common is to share computer graphic presentations, such as a POWERPOINT® slide presentation where a user shares his or her slide presentation with others in the conference. The parties can also share video images. The operator uses the available conferencing system and Super Video Graphic Array (SVGA) as a method of viewing these video signals to document and provide camera images on the user's computer or laptop.

Past videoconferencing systems have many disadvantages, including but not limited to, if a participant has a question on a slide or aspect of the presentation, the presenter must control the images to scroll back to the location in question and must toggle through the slide presentation to answer the participants' question. Also, in most conferencing systems, the presenter has control over the presentation, and the participant has no control over what other participants can view.

Recently many inventors have seen the need to allow a plurality of clients or users to collectively collaborate on presented work. These systems allow two or more users of the internet to move or modify Hyper Text Markup Language (HTML) documents with referring to the same. These systems work with browsers and web sharing managers provided in the shared client computer system of a source and receiver, and are constructed in such a manner that the web sharing manager of the shared client computer system of the receiver can receive the event message of the source from the web sharing manager of that source. Accordingly the event message is shared by the source and receiver, and the displaying and controlling of the same web page are simultaneously realized on the shared client computer system. Even further still, as incorporated by reference U.S. Pat. No. 7,310,657 to Nakamura describing in summary, a computer system comprising a plurality of user systems connected to each other being adapted to display a work area on a display screen, alternatively a plurality of users' systems connected to each other through a computer network. In Nakamura user systems include: collaboration work controller having a user management table for registering a node identification code given for each of the user systems and owner identifier related to the node identification code, and an object management table for registering object information related to the node identification code; and an obtainer for obtaining, based on an event entry for an object, the node identification code related to the object by referring to the object management table, obtaining the owner identified related to the obtained node identification code by referring to the user management table, and displaying the object on the screen in the manner that the obtained owner identifier can be discriminated from owner identifiers of other objects. Nakamura shows a display screen where users are participating and collaborating in work drawing annotations simultaneously. The owner identifier identifies the user for each object the owner identifier is displayed to the user watching the display screen with the entry (drawing) of the object from the other user. In other words the owner can be identified; it is possible to identify the owner of the object of the collaborative work easily. Each system runs from each system and does not work from a server but merely each computer runs individually over a network.

However, in past systems the computer arrangement can be summarized as a plurality of users systems connected to each other, each being adapted to display a work area on a display screen or connected through a computer network. Collaboration of work is done on each system by use of a management table for registered node identification codes given for each system user. That is, every computer system, or one system, requires (as in Nakamura) storage of collaboration user identifier in at least one of the user's computer system. The inventor of this novel device and method of concurrently collaborative communications for use with medical imagery has improved upon the past art by allowing a server to have master control allowing for faster and more efficient performance as well as allowing for a collaboration with medical images in Digital Imaging and Communications in Medicine, hereinafter referred to as DICOM, environment.

The DICOM Standard pertains to the field of medical informatics. The DICOM Standard is well known in the arts and facilitates interoperability of medical imaging equipment by specifying a set of protocols to be followed by devices claiming conformance to the standard. The DICOM Standard outlines syntax and semantic of commands and associated information which can be exchanged using these protocols. For media communication, a set of media storage services to be followed by devices claiming conformance to the DICOM Standard, as well as file format and medical dictionary structure to facilitate access to the images and related information stored on interchange media. DICOM data file format is data formatted in groups of information, known as Data Sets. The DICOM Standard provides a means to encapsulate in a single file format structure the Data Set related to a DICOM information object. The DICOM Standard requires a single file format structure, as the DICOM Standard specifies that each DICOM file contain both File Meta Information and a properly formatted Data Set (as specified in DICOM Standard 3.10). The DICOM Standard further specifies that the byte stream of the DICOM Data Set be placed into the file after the DICOM File Meta Information (as specified in PS 3.10 DICOM Part10: Media Storage and File format for Media Interchange).

The DICOM Standard specifies the rules for encapsulating DICOM Data Sets in the requisite DICOM File format. The DICOM Standard requires that a file meta information header be present in every DICOM file, and that the file meta information includes identifying information of the Data Set (PS 3.7-1). The DICOM Standard requires that the Data Set conform to the service-object pair (SOP) Class specified in the file meta information. "The DICOM File format provides a means to encapsulate a File the Data Set representing a SOP Instance relating to a DICOM Information Object." The DICOM Standard provides for the encapsulation of waveform data (PS 3.5 Part 5: Data Structures and Encoding), and for the encapsulation of structured reports (Supplement 114: DICOM Encapsulation of Clinical Document Architecture Documents) within imagery bit streams to facilitate the interchange of information between digital imaging computer systems in medical environments.

The DICOM File Meta Information includes identifying information on the encapsulated DICOM Data Set. The DICOM Standard requires that a file header of identifying information be present in every DICOM file. The DICOM file header consisting of a 128 byte File preamble, followed by a 4 byte DICOM prefix, followed by the File Meta Elements. This means, for example, that a DICOM file of a chest x-ray image actually contains the patient identification within the file, so that the image can never be separated from patient information by mistake. A DICOM file contains both the image and a large amount of patient information about whom, where, and how the image was acquired, known in the arts as patient metadata.

However, DICOM files often contain little information about the content of the imagery or meaning of the imagery pixels, the encapsulated waveform data used for audio clinical notes, or the encapsulated structured reports used for clinical documents, all of which are used for clinical detection, diagnosis and treatment of disease. This network systems apparatus improves upon and applies in a collaborative environment which provides for capture, retrieval and concurrent viewing of both live and archived medical imagery streams for communication, collaboration and consultation with one or more sources of streaming imagery data by one or more users, also known as participant clients. Collaborated medical imagery streams comprise one or more sources of streaming imagery data, including DICOM imagery files. As used herein, DICOM imagery files include modality information objects, (e.g. streaming video), waveform information objects (e.g. voice audio, echocardiogram), and structured report document information objects (e.g. clinical documents), as specified in PS 3.3 Part 3: Information Object Definitions of the DICOM Standard.

Medical imagery streams include DICOM imagery files. This network systems apparatus allows for each user to collaborate simultaneously with all users viewing every other users' work product, as the work product is being created, all coincident with one or more streams of streaming imagery data wherein a server manages streams of medical imagery together with participant client input illustrations for use with DICOM imagery files. The network systems apparatus provides live video and audio communication, as well as a method of viewing, recording and transmitting streaming imagery data, which include DICOM imagery files, in DICOM format, which requires a single file format structure. Streaming imagery data includes both live and archived imagery data. As used herein, multi-channel streaming imagery data is defined as a collection of one or more sources of streaming imagery data each of which comprise at least one image frame that defines a time progression of output from various sources, which include video, encapsulated waveform data, and encapsulated structured reports.

The network systems apparatus provides multi-channel capability for capture, retrieval and concurrent viewing of both live and archived medical imagery streams for communication, collaboration and consultation with one or more sources of streaming imagery data by participant clients. Participant client input illustrations as defined herein include, but are not limited to telestrations, drawings, sketches, text annotations, including letter character text and numeric character text, voice annotations, video annotations, haptic annotations, patient metadata, and appended patient metadata. The network systems apparatus appends participant client input illustrations to streaming imagery data and encapsulates and saves those input illustrations, together with streaming imagery data, and relevant imagery metadata, including appended imagery metadata, from the collaboration session in a single file format structure, known as collaborated imagery files. The 'single file encapsulate and save' functionality of the network systems apparatus encapsulates and saves collaborated imagery files in a single file format structure, as may be required by standards for clinical documentation or medical records storage, including as specified in the DICOM Standard (e.g. as DICOM files).

The network systems apparatus appends metadata tags to participant client input illustrations and encapsulates those tagged input illustrations together with the Data Set from the streaming imagery data and relevant metadata information from the metadata header in a single file format structure for use within a DICOM imagery environment, including as specified in the DICOM Standard. The network systems apparatus appends metadata tags to voice annotations, video annotations, haptic annotations and clinical documents and encapsulates those voice annotations, video annotations, haptic annotations and clinical documents and saves those as DICOM files. The network systems apparatus can also append annotation files encapsulated as DICOM files to the Data Set for streaming imagery data, and encapsulate them together with relevant metadata information from the metadata header for streaming imagery data, and save in a single file format structure as collaborated imagery files (CIF).

Collaborated imagery files, also known as CIFs, conform to the DICOM Standard and can be stored, archived, queried, and retrieved as DICOM files. CIFs can be stored locally in media libraries and later retrieved for subsequent use in collaboration sessions. CIFs conform to the DICOM Standard [3.10] and can be encrypted and/or transmitted over networks for remote viewing, communication and collaboration. CIFs conform to specifications of the DICOM Standard for secure encapsulation of DICOM objects in a clinical document architecture (CDA). As such CIFs can be stored in archives conforming to health level seven (HL7), integrating the healthcare enterprise (IHE), cross-enterprise document sharing (XDS), cross-enterprise document sharing for imaging (XDS-I), Extensible Markup Language (XML).

CIF's can also encapsulate and save haptic imagery and annotations in COLLADA-compliant dae files. COLLADA (collaborative design activity) is an interchange file format for interactive 3D applications, that has been adopted by ISO as a publicly available specification, ISO/PAS 17506. COLLADA defines an open standard XML schema for exchanging digital assets among various graphics software applications that might otherwise store their assets in incompatible file formats. COLLADA documents that describe digital assets are XML files, usually identified with a .dae (digital asset exchange) filename extension.

CIFs conform to specifications of the DICOM Standard for encapsulation of audio with imagery data sets. CIFs conform to specifications to the DICOM Standard for DICOM structured reporting. CIFs can be viewed as stand-alone medical imagery, or embedded into other CIFs as video, audio and haptic annotations. The network systems apparatus can create collaborated imagery studies, also known as CIS's, which include one or more collaborated imagery files, encapsulated and saved in a single file format structure, as may be required by standards for clinical documentation or medical records storage, including as specified in the DICOM Standard format. Collaborated Imagery Studies, also known as 'Clini-DOCx' are visual story boards can be used for capture, display, file exchange, publication and distribution of collections of medical dicom vismemes.

The DICOM Standard defines the characteristics of a medical study performed on a patient as, "a collection of one or more series of medical images, presentation states, SR documents, overlays and/or curves that are logically related for the purpose of diagnosing a patient. Each study is associated with exactly one patient" (PS 3.3 A.1.2.2 STUDY IE). Streaming imagery data can include both collaborated imagery files and collaborated imagery studies. Both CIFs and Clini-DOCx can be incorporated into medical image streams of live or archived streaming imagery data for use during synchronous or asynchronous collaboration sessions.

The traditional way of capturing an image on a medical imaging apparatus commonly called a modality, generally consisted of an operator or technician first conducting a scan. Then, using the modality to save the image, in still or motion video format, into the modality memory or into a main image storage database. The next step in the process typically involved downloading the image into a hospital database, known in the arts as a Picture Archiving and Communications System, hereinafter referred to as PACS or PACS server. PACS is a medical imaging technology which provides economical storage of, and convenient access to, images from multiple modalities (source machine types). Electronic images, including patient information known in the arts as patient metadata, are transmitted digitally to and from PACS, eliminating the need to manually file, retrieve or transport film jackets. The universal form of PACS image file storage and transfer is the DICOM Standard, and is well known in the arts. PACS can be further defined by a storage and management system for medical images.

In the medical field, images such as x-rays, MRI's and CAT scans typically require a greater amount of storage than other images in other industries. A clinician would access the PACS system to retrieve the image, view and review the image, and conceivably develop a diagnosis based on the information from the image. This system imagery is viewed by a user and diagnosis made without image delay and the user accomplishes all these tasks live. "Live" referring to events simulated by a computer at the same speed that they would normally occur in real life. In graphics animation, for example, a live program (such as this inventor's system) would display objects moving across the display at the same time they would actually move, or in the case of this invention, a collaborant views the image live and collaborates from collaborant to collaborant with no perceivable delay to any of them.

A Tele-Visual Imagery Informatics Management System is hereinafter referred to as TIMS. The Applicant's network systems apparatus is known as the TIMS Clini-Pod Clinical Network System. It is comprised of three essential components: one called a TIMS Clini-Pod Clinical Network Server (CNS); another called a TIMS C2I2 Clini-Port [C2I2: Communication-Collaboration-Imagery-Informatics]; and a third called a TIMS Clini-Dock, as depicted in FIG. 1.

The TIMS Clini-Pod Clinical Network Server (CNS) is a computer that manages users, security, authentication, authorization, image streams, channels and sessions within the TIMS Clini-Pod Clinical Network System (i.e. this invention described herein) that allows for multiple users in multiple locations to concurrently collaborate on the images, each user to input highlighted graphic electronic traces and annotations over the medical image and single file each and all participant client input illustrations, which include telestrations, drawings, and annotations together with streaming imagery data, and relevant imagery metadata, including appended imagery metadata, from the collaboration session in a single file format structure, known as collaborated imagery files as may be required by standards for clinical documentation or medical records storage, including as specified in the DICOM Standard. DICOM compliant files must contain both imagery data sets and metadata information.

The TIMS Clini-Pod Clinical Network Server (CNS) manages the master control functionality of the TIMS Clini-Pod Clinical Network System. This functionality is achieved via the connection of the TIMS Clini-Pod Clinical Network Server (CNS) to the TIMS Clini-Dock and allows multiple users in multiple locations to view live all telestrations, and annotations from each of the users during the collaboration session as illustrated in FIG. 1. The telestrations and annotations are added as appended layers over the source video and do not alter the source imagery. In addition, when multiple TIMS Clini-Docks are connected to multiple medical modalities, as shown in FIG. 1, the TIMS Clini-Pod Clinical Network Server (CNS) enables the concurrent collaboration with each and all of these multiple sources of streaming imagery data. The TIMS Clini-Pod Clinical Network Server (CNS) dynamically controls which of the multiple sources of streaming imagery data each TIMS C2I2 Clini-Port wishes to view, as depicted in FIG. 3.

TIMS Clini-Pod Clinical Network Servers (CNS) come in three varieties: Pod or pair, typically 1-2 Pods (hub-n-spoke or peer-2-peer); Quad, or team [typically 2-4 Pods); and Squad, or hive (typically four Quads, or 16 Pods). Local CNS network servers connect individual collaborants, also known as pod team members' to devices in their Clini-Pod, as depicted in FIG. 13. Team CNS network servers interconnect four Clini-Pods each other to allow for four-party tele-visual communication and live synchronous collaboration with shared work products, as depicted in FIG. 14. Hive CNS network servers connect four or more team network servers as depicted in FIG. 15. Clini-Pod Network Servers can be deployed in hub-and-spoke, sonnet ring, cluster, mesh or chord, or any other network configuration, as described in the Bellcore Telecommunications Management Network architecture [TMN].

The TIMS C2I2 Clini-Port software application allows participant clients to add other sources of streaming imagery data by selecting the "add+" channel selection tab, and viewed on the channel tabs of the multi stream viewer as shown in FIG. 3, (channel 1X . . . ). The multi-channel stream view capability of the TIMS C2I2 Clini-Port software application allows concurrent viewing of multiple channels of both live and archived medical imagery streams as depicted in FIG. 7. The multi-channel stream view selection capability is depicted in FIG. 9, and again in FIG. 10 with multiple channels of both live ("stream") and archived (image "81420095249.jpg, and image "99200982617.mpg") medical imagery streams selected for capture, retrieval and concurrent viewing during a collaboration session. The TIMS C2I2 Clini-Port software application includes DICOM view capability, which allows participant clients to view, communicate, collaborate and consult with DICOM imagery streams. The TIMS C2I2 Clini-Port software application includes capability to view non-DICOM imagery as well, which allows participant clients to view, communicate, collaborate and consult with non-DICOM imagery streams. The multi-channel stream view capability of the TIMS C2I2 Clini-Port software application allows participant clients to capture, retrieve and concurrent view both live and archived medical imagery streams for communication, collaboration and consultation with one or more sources of streaming imagery data by one or more participant clients, with both DICOM and non-DICOM imagery streams during a collaboration session. Each participant client, some of whom may be located remotely to the imaging modalities, is able to view, analyze, discuss and comment on each of the participant client input illustrations concurrently live and save such analysis or discussion as may be clinically relevant.

In one embodiment, the connection of the TIMS Clini-Pod Clinical Network Server (CNS) to the TIMS Clini-Dock allows a TIMS C2I2 Clini-Port to customize preferences for capture, retrieval, and viewing of streaming imagery data while the patient is still on the examination table. A TIMS C2I2 Clini-Port can have direct access and control of the streaming imagery data and maintain the native resolution and frame rate output from the medical modality. If desired, a TIMS C2I2 Clini-Port can adjust the native resolution, frame rate, and compression of the streaming imagery data specific to the user's preferences. In addition, a TIMS C2I2 Clini-Port is able to instruct in live, a clinician who is controlling the streaming imagery data at the modality, and view the results of those instructions to ensure that imagery acquired is consistent with user preferences, as depicted in FIG. 3. Those instructions are conveyed via two way communication between user and clinician with voice, text, video or telestrations within the TIMS Clini-Pod Clinical Network System and are not reliant upon any external communications network.

Without access to this master control of the TIMS Clini-Dock by the TIMS Clini-Pod Clinical Network Server (CNS), imagery viewed by a remote client using another invention is limited to the quality of the view and capture settings specified by others, which may be different than those desired or required by the remote client. TIMS Clini-Dock is a multichannel stream or stack to allow live capture and archived retrieval for (1) tele-visual communications modalities: (1) streaming video; (2) medical imagery and waveforms; (3) electronic medical records; and (4) clinical and genomic maps and interactive biometric data visualizations.

As used herein, "streaming medical imagery" includes all information objects described in the DICOM Standard, including images, video, modality imaging and waveform—audio, visual and haptic, medical records and clinical documents, phenotypic and genomic maps, as described in the Institute of Medicine's *Towards Precision Medicine—A New Taxonomy of Disease*; and for biometric data visualizations from connected medical devices, signals and sensors used for local and remote patient monitoring.

TIMS Clini-Docks are typically deployed in four (4) dual channel streamer stacks to accommodate both live and archived streaming imagery data from these four principal modalities for tele-visual communications and collaboration with imagery informatics. Clini-Dock streamer Channel (1) is typically reserved for video communications and conferencing among team members and other collaborants. Channel (2) normally designated for electronic medical records and patient monitoring; Channel (3) for medical imaging modalities and wave forms. Channel (4) for data mapping and interactive biometric data visualizations, including virtual reality and augmented reality displays. The TIMS C2I2 Clini-Port typically has one or more multi-channel monitors for connected devices, which can be situated locally, within the Clini-Pod, or at remote locations, including other Clini-Pods.

The TIMS Clini-Dock, due to its novel capabilities, can acquire analog or digital video signals, standard or non-standard video resolutions, medical or non-medical imagery, live or archived imagery, and compressed or uncompressed imagery formats. The TIMS Clini-Dock converts analog sources of streaming imagery data, as well as non-standard sources of streaming imagery data into digital imagery data sets for use by participant clients during collaboration sessions. The TIMS Clini-Dock can also convert non DICOM digital imagery data sets, including non DICOM modality imaging (e.g. video), waveform data (e.g. voice, audio, haptic), and structured reports (DICOM-SR from PACS) and clinical documents (CCD, CCR from EHR medical records systems) into DICOM imagery streams for use by participant clients during collaboration sessions. The TIMS Clini-Dock stack depicted in FIG. 1 allows for capture of multiple sources of streaming imagery data in any and all combinations of the preceding specifications, (e.g. both DICOM and non-DICOM imagery streams, standard and non-standard imagery streams, and compressed and uncompressed imagery streams) and allows TIMS C2I2 Clini-Ports concurrent viewing of multiple sources of streaming imagery data. The TIMS Clini-Dock is a medical device that processes any video output from a video source into an image stream, including but not limited to streaming imagery data from medical modalities, as depicted in FIG. 1.

In one embodiment the invention provides for a unique stream-splitter-server-router functional combination in a single server core device having bi-directional communications capability with other Pod server cores via network, video and wireless connectivity. This embodiment allows for dynamic neurosynaptic connectivity for multichannel multiplexed networked visual communications.

A medical imagery stream is defined as a collection of one or more sources of streaming imagery data which comprise at least one image frame that defines a time progression of output from a video source. The TIMS Clini-Dock maintains image quality from source modalities as required for conformance to DICOM Standards for clinical use. The TIMS Clini-Dock streamer has secured regulatory clearances for transmission and viewing of medical imagery streams for clinical diagnostic purposes.

In one embodiment, the TIMS Clini-Pod Clinical Network Server (CNS) provides the live video and audio communication, as well as a method of recording, transmitting and saving images in a single file format structure, including as specified in DICOM Standard. DICOM is a medical imaging standard common in the medical industry. DICOM can also be defined as a standard in the field of medical informatics for exchanging digital information between medical imaging equipment (such as radiological imaging) and ensuring interoperability with other systems. DICOM, including protocols for device communication over a network, syntax and semantics for commands and associated information that can be exchanged using protocols, a set of storage services and devices claiming conformation to the standard, as well as file format and medical directory structures to facilitate access to images and related information stored on media that shares information. The embodiment can serve as the connection point between any medical imaging modality and a hospital PACS, medical archive or other image repository, including clinical data repositories, personalized clinical knowledge repositories, medical dicom vismeme vaults and metadata repositories.

One component of this invention, the TIMS Clini-Pod Clinical Network Server (CNS), is able to connect DICOM equipment and older non-DICOM equipment to a hospital network, allowing imaging studies to be stored and saved. The TIMS Clini-Pod Clinical Network System, this invention described herein, briefly described as a trace overlay and annotation system that users can collaborate with each other live, each viewing each other's object inputs and those object inputs can be encapsulated and saved in a single file format structure, including as specified in DICOM Standard, in PACS, in a DICOM compliant image archive, or in other image repositories.

Another embodiment the TIMS Clini-Pod CNS network system can be deployed as collaboration portals for multi-party clinical collaboration among specialist providers; care coordination for caregiving teams both local and remote; and patient provider engagement, the support of meaningful use goals and objectives for electronic medical records. Clini-Pod CNS also support health information exchange for integrated delivery systems; for biomedical, clinical and genomic mapping and interactive data visualizations, as well as clinical decision support for value care-giving teams.

Still other embodiments provide networked informatics connectivity for medical kiosks, offices and retail clinics, ambulatory care and nursing facilities. Often these facilities have limited connectivity for access to hospital-based electronic medical systems. In those circumstances the TIMS Clini-Pod CNS as "LAND" [Local Adapter for Network Distribution] and "SEE" [Surrogate Electronic Health Record Environment] to facilitate health information exchange with hospitals and other caregiving facilities as depicted in FIG. 26.

Use of TIMS Clini-Pod access and enable groups with access to EHR systems to share electronic medical information with those who do not, and specifically by health information exchange with Consolidated Clinical Document Architecture (C-CDA") compliant documents, including Continuity of Care Documents (CCD, CCD+, etc), Fast Healthcare Interoperability Resources ("FHIR") and Universal Transfer Forms (UTF.)

The inventor has developed a novel and simple network systems apparatus and method of using the same, to allow a group of persons to concurrently collaborate on a computer system, with each participant viewing each other's telestrations, drawings, and annotations and saving them together with streaming imagery data, and relevant imagery metadata, including appended imagery metadata and saving them together in a single file format structure as may be required by standards for clinical documentation or biomedical records storage, including those as specified in the DICOM, C-CDA and FHIR Standards for interoperable health information exchange.

SUMMARY

The invention relates generally to a multimedia collaborative conferencing system and method of using the same for generating input illustrations, which include telestrations, drawings and annotations on medical images concurrently with other users and saving the participant client input illustrations with streaming imagery data, and relevant imagery metadata, including appended imagery metadata in a single file format structure, including as specified in the DICOM Standard. The network systems apparatus in this invention is the TIMS Clini-Pod Clinical Network System. It is comprised of three essential components, one called the TIMS Clini-Pod Clinical Network Server (CNS), another called the TIMS C2I2 Clini-Port, and a third called the TIMS Clini-Dock.

The TIMS Clini-Dock includes a medical image acquisition system adapted for receiving and transmitting medical images, constructed from, a computer having communications capability adapted for acquisition and transmission of a plurality of medical imaging and video signals. Wherein the medical image and video signals are acquired at the medical device's native resolutions, transmitting the signals at their native resolutions and native frame rates to a receiving device, receiving the medical imaging video signals in analog or digital form, and if required, compressing and scaling the signal, converting the signal to digital form for transmission, and transmitting the digital signals using secure encryption protocols a display device. The TIMS Clini-Dock is capable of concurrently acquiring signals from a plurality of medical imaging systems, as depicted in FIG. 1, including but not limited to, ultrasound, Computer Tomography (CT) scan, fluoroscopy, endoscopy, magnetic resonance imaging, nuclear medicine, echocardiogram ultrasound and microscopy. Medical imaging equipment is also referred to as modalities. A more complete list of sources for DICOM imagery streams can be found in the DICOM Standard [PS 3.3 Part 3: Information Object definitions], which include video (imaging), audio (waveform), and clinical documents (structured reports).

The TIMS Clini-Dock can also receive the video image signal from a plurality of video sources, including but not limited to, S-video, composite color and monochrome, component red blue green video (RGB, three additive primary colors), Digital Visual Interface (DVI), any video transport protocol including digital and analog protocols, high definition multimedia interface (HDMI, compact audio video interface uncompressed digital data), serial digital interface (SDI), and DICOM video in their native, enhanced or reduced resolutions or their native, enhanced or reduced frame rates. The component, known in this invention as the TIMS Clini-Pod Clinical Network Server (CNS), manages the communication between all acquisition systems (TIMS Clini-Docks), between all users (TIMS C2I2 Clini-Ports), between the hospital site server, located on site or remotely, that stores the hospital's images, and the hospital network in both local area and wide area configurations.

The TIMS Clini-Pod Clinical Network Server (CNS) manages both live and archived streaming imagery data acquired from the TIMS Clini-Docks, and archived imagery, including collaborated imagery files, retrieved in a predetermined digital single file format structure, including as specified in DICOM Standard, and stored locally in media libraries on a participant client computer storage devices, on the tele-visual imagery informatics management system server, on the picture archiving and communications system server, or other digital imaging and communications in medicine compliant repository, or on any other repository that requires streaming imagery data and metadata to be combined in a single file format, including clinical data repositories, personalized clinical knowledge repositories, medical dicom vismeme vaults and metadata repositories.

A participant or user computer can be defined as typically made of several components such as a main circuit board assembly having a central processing unit, memory storage to store programs and files, other storage devices such as hard drives, and portable memory storage, a power supply, a sound and video circuit board assembly, a display, and an input device such as a keyboard, mouse, stylus pen and the like allowing control of the computer graphics user interface display, where any two or more of such components may be physically integrated or may be separate. In one depiction, a remote location communicates with the networked computer, for the purpose of collaborating and conferencing with medical streaming imagery data.

A network systems apparatus and method for using the same for concurrent collaboration between users, collaborating by a variety of input illustrations, which include video, audio, telestrations, drawings and annotations, as well as collaborating on medical images that are typically accessed on a storage server database, imaging archives, or continuous streaming video. A TIMS Clini-Dock is connected directly to multiple sources of streaming imagery data, as depicted in FIG. 1, and continuously streams images to the TIMS server. Any number of TIMS C2I2 Clini-Ports can request information from the TIMS Clini-Pod Clinical Network Server (CNS). Each TIMS C2I2 Clini-Port in a conference with another or other TIMS C2I2 Clini-Ports can view all the TIMS C2I2 Clini-Port object inputs as they occur. A TIMS C2I2 Clini-Port includes a user, typically a person who has interest in using the system for medical review and diagnosis of patient image data.

The TIMS Clini-Pod Clinical Network Server (CNS) keeps track of all TIMS Clini-Docks that have image streams available and displays a list of image streams available TIMS C2I2 Clini-Ports, as depicted in FIG. 3. The TIMS Clini-Pod Clinical Network Server (CNS) communicates with image repositories, including but not limited to a PACS system, and stores information on all TIMS C2I2 Clini-Port's computers live. The TIMS Clini-Pod Clinical Network Server (CNS) includes software components that: manage streaming requests to the TIMS Clini-Dock; manage authentication and authorization tasks for access and privileges; manages users information, roles, session logs and, configurations for the TIMS Clini-Pod Clinical Network Server (CNS) and TIMS Clini-Docks; manage web services interactions with TIMS C2I2 Clini-Ports; send, query and retrieve collections of one or more streaming imagery data files, including collaborated imagery files, also known as studies to and from image repositories, as depicted in FIGS. 10 and 11, including but not limited to DICOM compliant image repositories, e.g. PACS; specify unique combinations of image quality, resolution, compression and frame rates as may be required for each collaboration session, as depicted in FIG. 3; access patient information from a DICOM Modality Worklist utility (DMWL); collaborated imagery files, to the TIMS C2I2 Clini-Ports; manage text chat information; manage DICOM send services, wherein the DICOM send service sends the annotated images to PACS or a DICOM compliant image repository, known as medical image archives as depicted in FIG. 10; allow for query and retrieve functionality that retrieves the list of DICOM studies from PACS server and DICOM compliant repositories and sends the studies to TIMS C2I2 Clini-Ports.

A DICOM study is defined as a collection of one or more medical images and patient data combined in a single file format structure, including as specified in the DICOM Standard.

DICOM Modality Worklist is defined as a software utility that invokes DICOM query and retrieve functionality which enables imaging equipment (e.g. medical modalities) to query medical image stores, including but not limited to PACS, and obtains details of patient and scheduled examinations electronically, including patient demographics and study data, avoiding the need to type patient information multiple times, as depicted in FIG. 10. Clini-Pod typically deploy with Clini-CDR (Clinical Data Repositories, consisting of p-CKR [personalized Clinical Knowledge Repositories] with local storage of CIFs and medical dicom vismemes in p-CKR vismeme vaults; and a metadata repository which houses reference links to collaborated imagery files, along with Dicomized security tokens which provide granular control over access to shared imagery files stored in clinical data repositories, personalized clinical knowledge repositories, medical dicom vismeme vaults and metadata repositories.

The TIMS Clini-Pod Clinical Network Server (CNS) also manages all the participant client input illustrations, specifically, the entire participant client input illustrations, sketches, drawings, telestrations and annotations. Participant client input illustrations as previously defined herein include, but are not limited to telestrations, drawings, sketches, text annotations, including letter character text and numeric character text, voice annotations, video annotations, haptic annotations, imagery metadata and appended imagery metadata, as depicted in FIG. 7. All participant client input illustrations are managed by the TIMS Clini-Pod Clinical Network Server (CNS) based on a file sharing scheme where new input illustrations keep getting appended to the file on the TIMS Clini-Pod Clinical Network Server (CNS). The TIMS Clini-Pod Clinical Network Server (CNS) distributes copies of streaming imagery data to each of the participant clients. Since participant clients collaborate only with copies of images, they do not alter the original streaming imagery data in any way. This approach of generating input illustrations on the TIMS Clini-Pod Clinical Network Server (CNS), and distributing only those input illustrations and not the underlying images to each participant client, significantly improves operating performance and reduces image latency and wait times. That method of moving images with illustrations back and forth from a computer to a server, results in losing illustration quality or consuming more bandwidth. However, with this novel invention, the process of multi-layer multi user input illustrations on any underlying images, including streaming imagery data, and updating and appending on the streaming imagery data without sacrificing network bandwidth is novel to this invention.

The TIMS Clini-Pod Clinical Network Server (CNS) allows TIMS C2I2 Clini-Ports to create collaborated imagery files synchronously or asynchronously. The TIMS Clini-Pod Clinical Network Server (CNS) uses a process of local registration to identify the image frames needed for viewing on each of the participant client computers, and sends to each of them only the image frames necessary for participation in a collaboration session. The TIMS Clini-Pod Clinical Network Server (CNS) enables each participant client to use a scalable window so all input illustrations for each and every participant client are dynamically ratio metric based on the underlying image aspect ratio of the respective participant client computer. Therefore, all the input illustrations always point to the part of the window and image as originally intended, regardless of window size on the clients computer display. A central frame counter originating in the participant client computer, which has play/pause control, issues frame synchronization commands to synchronize the image streams on all participant collaborants' computers. This method significantly reduces bandwidth requirements and improves responsiveness of system updates and appends. The client computer which has play/pause control also sends synchronizing commands whenever its displayed images are paused. This ensures that the same frame is available to all participating clients by broadcasting that pause frame number along with the pause command to all participating clients.

Client participants can receive video streams directly from the TIMS Clini-Dock using a local area network. The invention can also detect if a user has low bandwidth, in transmission, or in reception, or in both and can compensate by only sending selected image frames to that user. For example, with low bandwidth the TIMS Clini-Pod Clinical Network Server (CNS) can send every third, fifth, or Nth frame of a collaborated imagery to clients so that client does not have any perceptible delay. Remote client participants using the internet must receive all imagery from the TIMS Clini-Pod Clinical Network Server (CNS) for secure transmission, rather than directly from the TIMS Clini-Dock, to ensure streaming imagery data is not transmitted over the internet without encryption.

TIMS C2I2 Clini-Ports, also known as participant clients, can take several roles. Each participant client can capture, retrieve and concurrently view both live and archived streaming imagery data of their own choosing, including medical imagery streams selected for the collaboration session; capture, retrieve and concurrently view both live and archived streaming imagery data streams selected by other participant clients, including medical imagery selected for the collaboration session; each participant client can add multiple sources of streaming imagery data, also referred to as multiple channels, of both live and archived streaming imagery data for other participant clients to capture, retrieve and concurrently view; capture, retrieve and concurrently view multiple sources of both live and archived streaming imagery data, including medical imagery streams selected for a collaboration session; concurrently add input illustrations on both live and archived streaming imagery data; taking on any and all of the above roles dynamically, as depicted in FIG. 4.

In addition, the TIMS C2I2 Clini-Port software application is a collaborative, interactive; tool for synchronous or asynchronous media annotation, which can be used with medical files to enable participant clients to communicate, collaborate and consult with medical images for clinical review and discussions and deciding on relevant medical procedures.

The invention—combination streamer-splitter-server-router core—allows any of the TIMS C2I2 Clini-Ports to host a collaboration session with any other TIMS C2I2 Clini-Ports, including peer-2-peer, hub-n-spoke, mesh or chord network configurations, as depicted in FIG. 16. The host selects any number of participant clients from their contact list, as depicted in FIG. 5, and sends a request to those clients they wish to collaborate with. The participant client receiving the request can elect to join or decline the session by selecting the appropriate button on the dialog box that appears on their computer monitor, as depicted in FIG. 6. Upon acceptance of the request, the client's monitor is automatically switched to view the same imagery as the host. The host can select live streaming imagery data from any of the available TIMS Clini-Docks, as depicted in FIG. 3, can select from any archived streaming imagery data available through the query and retrieve functions, as depicted in FIG. 11, and concurrently collaborate with the selected streaming imagery data, live, archived or both, with all clients during the collaboration session.

All participant client input illustrations added are concurrently visible to all participant clients. In addition, each participant client can add input illustrations, which include telestrations, drawings, text annotations, voice annotations, video annotations, haptic annotations, to streaming imagery data, together with relevant imagery metadata, including appended imagery metadata. Furthermore, each client can also use the TIMS Clini-Pod Clinical Network System to chat with each other during a collaboration using a text chat facility. A separate text window box is displayed that allows for each participant client to instant message each other in text format and include those images as input illustrations, as depicted in FIG. 7. One feature of this invention is that the host can disable the edit control of any client, such that a particular client will not be able to add or edit the annotations or telestrations, as depicted in FIG. 8. At this point, the client can only view the annotations made by others. The host can also pass the control of the video stream start/stop/pause functions to another client. This control allows the host to enable or disable the functionality to all clients or selected clients and can be done at any time during the collaboration session. At the conclusion of the session, participant clients can encapsulate and save all input illustrations, which include telestrations, drawings and annotations together with streaming imagery data, and relevant imagery metadata, including appended imagery metadata, from the collaboration session, in a single file format structure, known as collaborated imagery files. Collaborated Imagery Files are encapsulated and saved in a single file format structure, as may be required by standards for clinical documentation or medical records storage, including as specified in the DICOM Standard (e.g. as DICOM files). Clients can send collaborated imagery files to any PACS or DICOM compliant image repository, including clinical data repositories, personalized clinical knowledge repositories, medical dicom vismeme vaults and metadata repositories. A session log is recorded and saved on the TIMS server, as depicted in FIG. 9.

The invention also works with wearable signals, sensors, devices and monitors-, collectively Personal Digital Assistant. Participants (PDA) clients can use these PDAs to view, consult and collaborate on DICOM images. Personal digital assistant is any small mobile hand held device that provides computing and information storage such as hand held computers, phones, media display devices and handheld computers, including watches and vision.

The principle preferred embodiment and modes of operation of the present invention have been described in the forgoing specification. The invention which is intended to be protected herein, however, is not to be construed as limited to the particular embodiments disclosed, since these embodiments are to be regarded as illustrative rather than restrictive. Variations and changes may be made by others without departing from the spirit of this invention. Accordingly, it is expressly intended that all such variation and changes which fall within the spirit and scope of the claims be embraced thereby.

BRIEF DESCRIPTION OF DRAWINGS

Other objects, features, and advantages will occur to those skilled in the art from the following description of an embodiment and the accompanying drawings, in which:

FIG. 5, shows a graphic user interface screen shot of client selecting participants to collaborate with.
FIG. 9, shows a graphic user interface screen shot of list of multiple collaboration sessions.
FIG. 17, depicts Value Chain Knowledge Exchange
FIG. 18, depicts Interactive Data Visualization Processes
FIG. 19, depicts Interactive Data Visualization Sensors
FIG. 20, depicts Interactive Data Visualization Slices
FIG. 21, depicts Knowledge Networks for Biomedical Research
FIG. 22, depicts Knowledge Networks for Precision Medicine
FIG. 23, depicts Patient-Centric Precision Medicine

DETAILED DESCRIPTION

Figure 1:
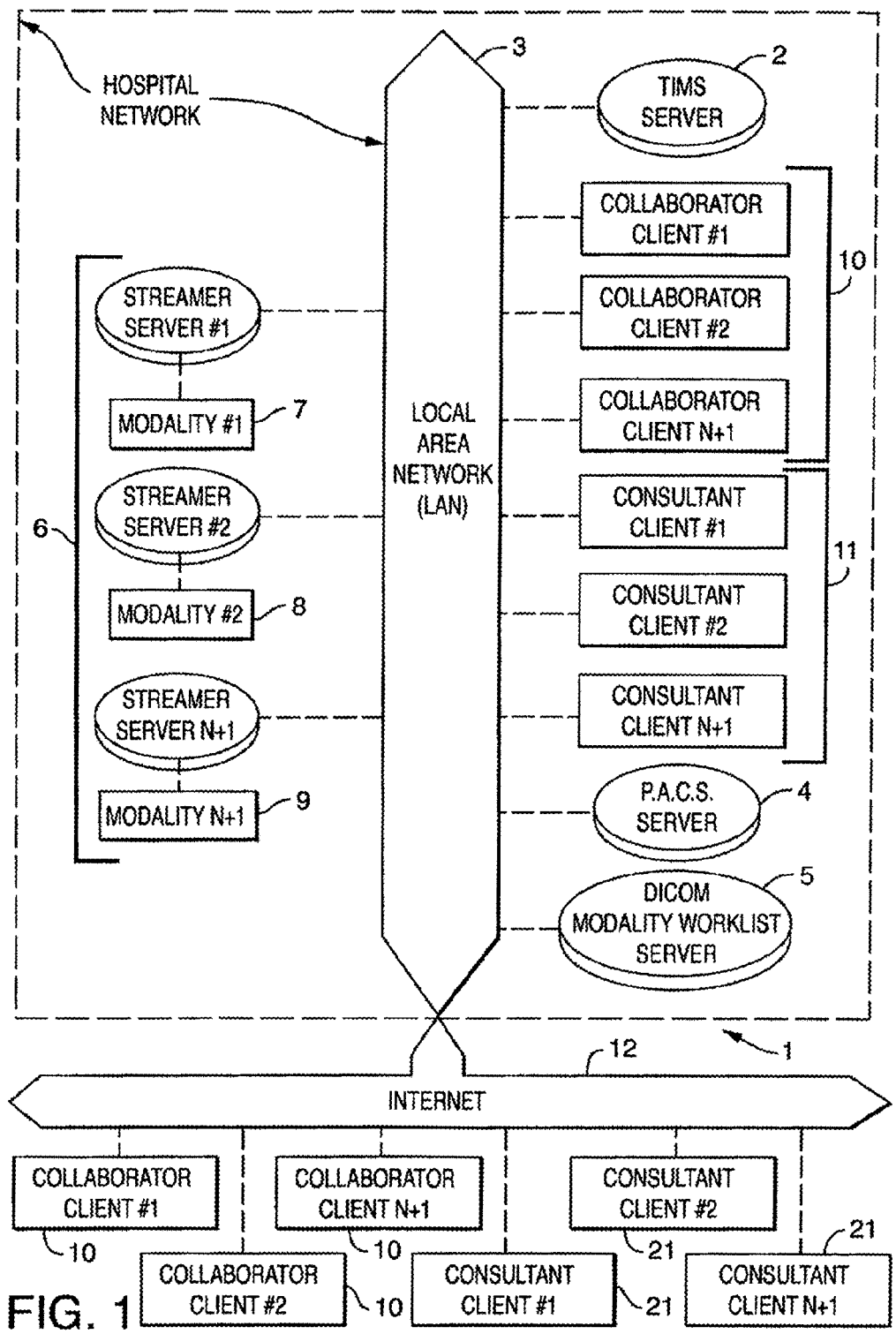
FIG. 1, shows a block diagram of the invention.
Figure 2:
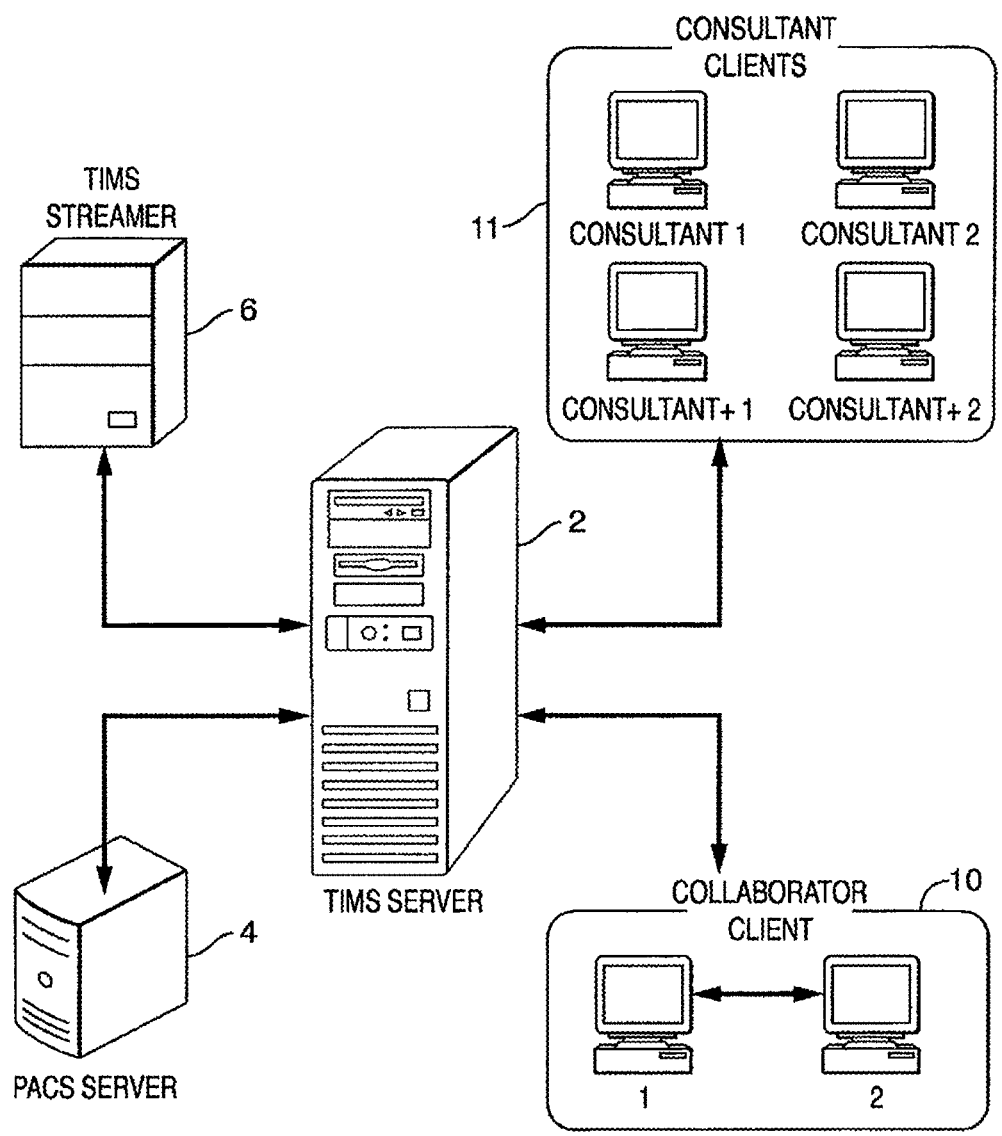
FIG. 2, shows a block diagram of a portion of the system.

A network systems apparatus 1 for allowing users to concurrently communicate live; concurrently collaborate live, and concurrently consult live while concurrently viewing multiple sources of streaming imagery data 13 on a display screen using sketched and annotated participant client input illustrations over streaming imagery data 13 among a group of remotely located participant clients 10.

The network systems apparatus having a TIMS Clini-Pod Clinical Network Server (CNS) 2 including associated data base in communication with a local area network 3, in some circumstances connected to and having access to a medical PACS server 4 including associated database all capable of using the protocols required by the DICOM Standard and all having access to a DICOM modality work list utility for appending imagery metadata 5 including associated database providing medical patient metadata. To collect streaming imagery data 13 the system together with at least one TIMS Clini-Dock 6 in contact with the local area network 3 wherein the TIMS Clini-Dock 6 is providing live streaming imagery data to the local area network 3 as it receives concurrent sources of live streaming imagery data 6 from multiple medical modalities 7,8,9 such as but not limited to, ultrasound, fluoroscopy and video. A participant client can view streaming imagery data 13 in a single file format structure, including as specified in the DICOM Standard together with participant client input illustrations 18 which include, telestrations 21, drawings 22 and annotations 234 (known as participant client input illustrations herein) over the streaming imagery data and saving that streaming imagery data, relevant imagery metadata, including appended imagery metadata together with participant client input illustrations 18 single file format structure, including as specified in a digital imaging and communications in medicine file structure in the media library on a local storage device, PACS 4 or other DICOM compliant image repository, or other repository that requires streaming imagery data and metadata to be combined in a single file format structure, including clinical data repositories, personalized clinical knowledge repositories, medical dicom vismeme vaults and metadata repositories.

This network systems apparatus allows for one or more TIMS C2I2 Clini-Ports 10 to concurrently use the apparatus at the same time. The network systems apparatus 1 also allows participant clients to concurrently collaborate live, as defined by this system. The plurality of TIMS C2I2 Clini-Ports can concurrently view multiple sources of live and archived streaming imagery data-13, and concurrently create input illustrations 18 over that streaming imagery data 13 which include telestrations 21, drawings 22 and annotations 23, as they are appended to that imagery, and encapsulate and save those participant client input illustrations, including telestrations, drawings, and annotations, together with streaming imagery data, and relevant imagery metadata, including appended imagery metadata, from the collaboration session in a single file format structure, known as collaborated imagery files. The network systems apparatus 1 'single file encapsulate and save' functionality encapsulates and saves collaborated imagery files in a single file format structure, as may be required by standards for clinical documentation or medical records storage, including as specified in the DICOM Standard, on the TIMS Clini-Pod Clinical Network Server (CNS) 2, on the media library on a local storage device, a PACS 4, or other DICOM compliant image repository, or on any other repository that requires streaming imagery data and metadata to be combined in a single file format structure, including clinical data repositories, personalized clinical knowledge repositories, medical dicom vismeme vaults and metadata repositories.

TIMS C2I2 Clini-Ports can retrieve archived collaborated imagery files for use during current or future collaboration sessions. TIMS C2I2 Clini-Ports can include collaborated imagery files in patient studies. In one embodiment, a collaboration session can include one or more participant clients that can utilize personal digital assistants (PDA) over the internet 12.

A method for allowing one or more participant clients to concurrently collaborate live on medical images 13, all participants clients running substantially the same TIMS C2I2 Clini-Port software application program on each of the participant client's computers; storing the program on each of the participant client's computers. Each participant client computer displaying the graphic user interface output 25 of that program on their computer display. Each participant client computer linking to each other and to the TIMS Clini-Pod Clinical Network Server (CNS) 2 using a local area network 3. All TIMS C2I2 Clini-Ports 10 have access to the local area network 3 and internet 12. The TIMS Clini-Pod Clinical Network Server (CNS) 2 providing authentication and authorization to each participant client wherein linking the participant client to a DICOM Modality Worklist utility 5, a PACS server 4 or other DICOM compliant image repository, or on any other repository that requires streaming imagery data and metadata to be combined in a single file format structure for viewing medical images 13, including clinical data repositories, personalized clinical knowledge repositories, medical dicom vismeme vaults and metadata repositories.

Streaming imagery data into a local area network 3 wherein the TIMS Clini-Dock 6 is connected directly to medical modalities 7,8,9 acquiring live streaming imagery data or archived streaming imagery data, streaming that imagery data to TIMS C2I2 Clini-Ports 10 via a local area network 3. TIMS C2I2 Clini-Ports 10 acquire lists 15 of available medical modalities 7,8,9 from a local area network 3. Included in this network is a TIMS Clini-Pod Clinical Network Server (CNS) 2 having an associated database, identifying each participant client and the streaming imagery data available to each participant client; identifying on each participant client the streaming imagery data that is available on each participant client's computer. Also, the local area network 3 can be connected to the internet 12.

Figure 3:
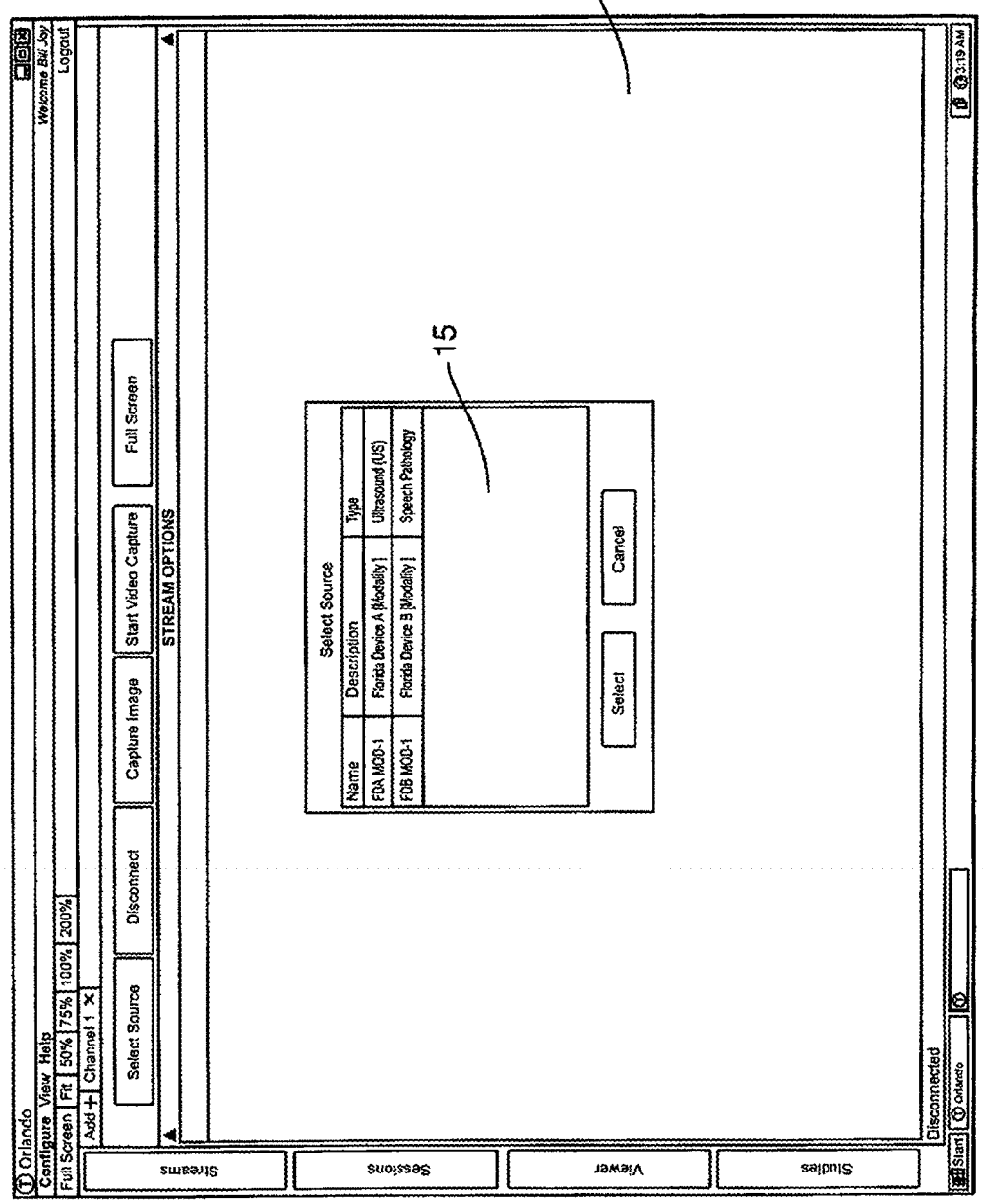
FIG. 3, shows a graphic user interface screen shot of client source select display.

When the participant client wants to view medical imagery and collaborate on that streaming imagery data with others, the participant client selects a channel on the multi-channel source selection tab for viewing streaming imagery data 15, 25 so he/she can initiate a collaboration session, as depicted in FIG. 3. When the participant clients are in a collaboration session, the TIMS Clini-Pod Clinical Network Server (CNS) 2 is providing updates to each participant client's computer at a rapid frame rate so each participant client's computer concurrently displays the same imagery. In other words, the TIMS Clini-Pod Clinical Network Server (CNS) 2 updates any changes to each and all of the streaming imagery data on each of the participant client's computers with synchronized signals sent over the local area network 3 dynamically such that all streaming imagery data on all participant client computer displays are the same, including sending each participant client's input illustrations 18, which include, telestrations 21, drawings 22, and annotations 23, and illustrations over the streaming imagery data 13 made by any of the participant clients 10.

The TIMS Clini-Pod Clinical Network Server (CNS) 2 with dynamic signal synchronization ensures that the same imagery refresh rate is concurrently available on all participant client computers. The TIMS Clini-Pod Clinical Network Server (CNS) 2 uses a process of local registration to identify the image frames needed for viewing on each of the participant client computers, and sends to each of them only the image frames necessary for participation in a collaboration session. The TIMS Clini-Pod Clinical Network Server (CNS) 2 enables each participant client 10 to use a scalable window so all input illustrations 18 for each and every participant client 10 are dynamically ratio metric based on the underlying image aspect ratio of the respective computer of each participant client 10. Each participant client 10 views what every other authorized participant client 10 in that session views.

The TIMS Clini-Pod Clinical Network Server (CNS) 2 distributes copies of streaming imagery data selected for use during a collaboration session to each of the participant clients. Since participant clients 10 collaborate only with copies of images, they do not alter the original streaming imagery data in any way. The TIMS Clini-Pod Clinical Network Server (CNS) 2 with dynamic signal synchronization allows at least one participant client 10 to telestrate 21, draw 22, annotate 23, input illustrations 18 over the streaming imagery data 13 in a concurrently collaboration session wherein a participant client 10 is telestrating 21, drawing 22, annotating 23 input illustrations 18 over the streaming imagery data 13. This approach of generating input illustrations 18 on the TIMS Clini-Pod Clinical Network Server (CNS) 2, and distributing only those input illustrations 18, and not the underlying images to each participant client 10, significantly improves operating performance and reduces image latency and wait times.

The TIMS Clini-Pod Clinical Network Server (CNS) 2 manages input illustrations 18 from all participant clients 10 in a concurrently collaborative environment with image streams which can include multiple streams of streaming imagery data. The TIMS Clini-Pod Clinical Network Server (CNS) 2 manages participant client 10 input illustrations 18, which include telestrations 21, drawings 22, and annotations 23 as they are appended to that imagery 13, and encapsulates and saves those participant client input illustrations 18, which include telestrations 21, drawings 22 and annotations 23 together with streaming imagery data 13, and relevant imagery metadata, including appended imagery metadata, from the collaboration session in a single file format structure, known as collaborated imagery files.

Figure 4:
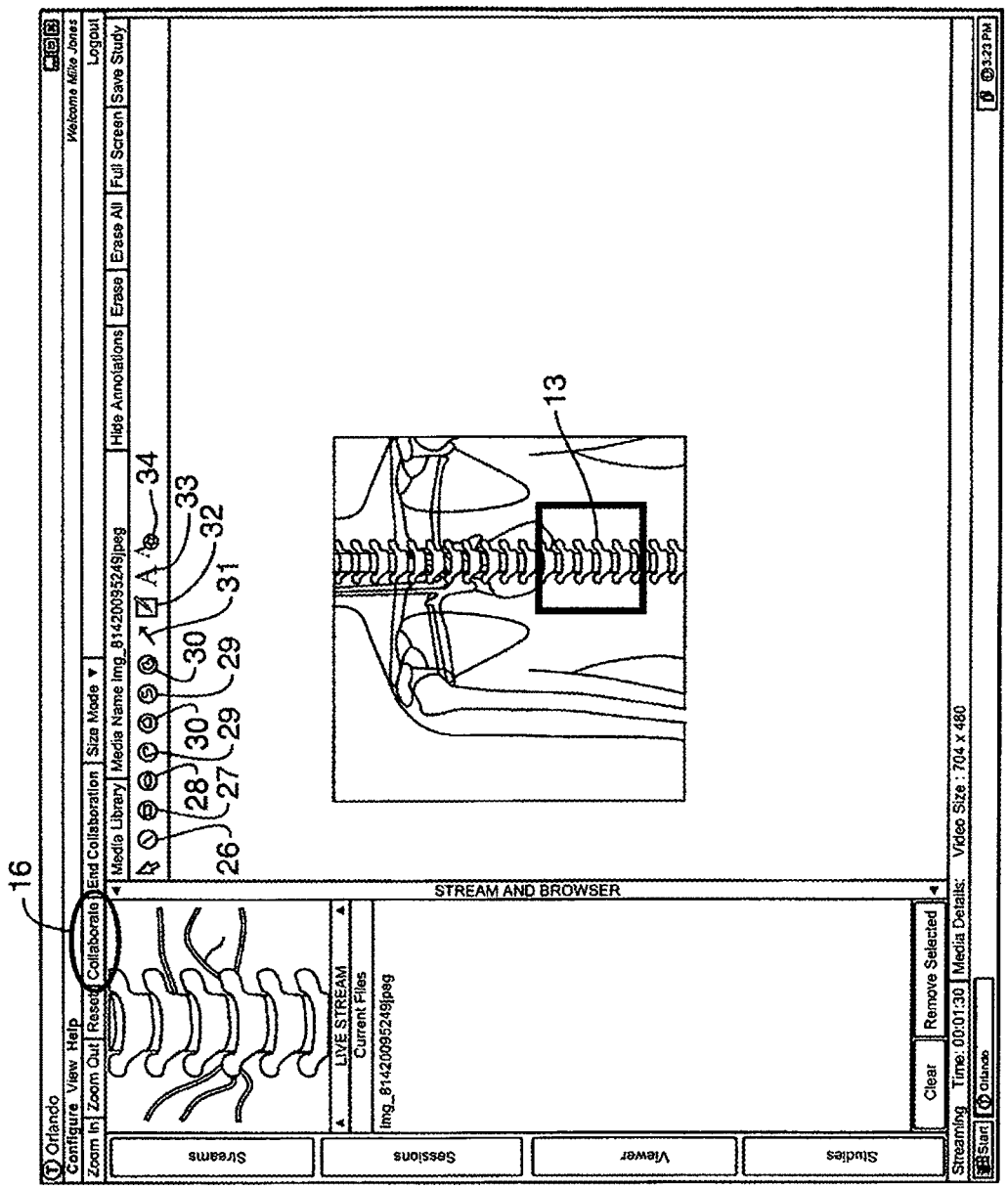
FIG. 4, shows a graphic user interface screen shot of client source image with illustration tool bar and collaborate function.
Figure 5:
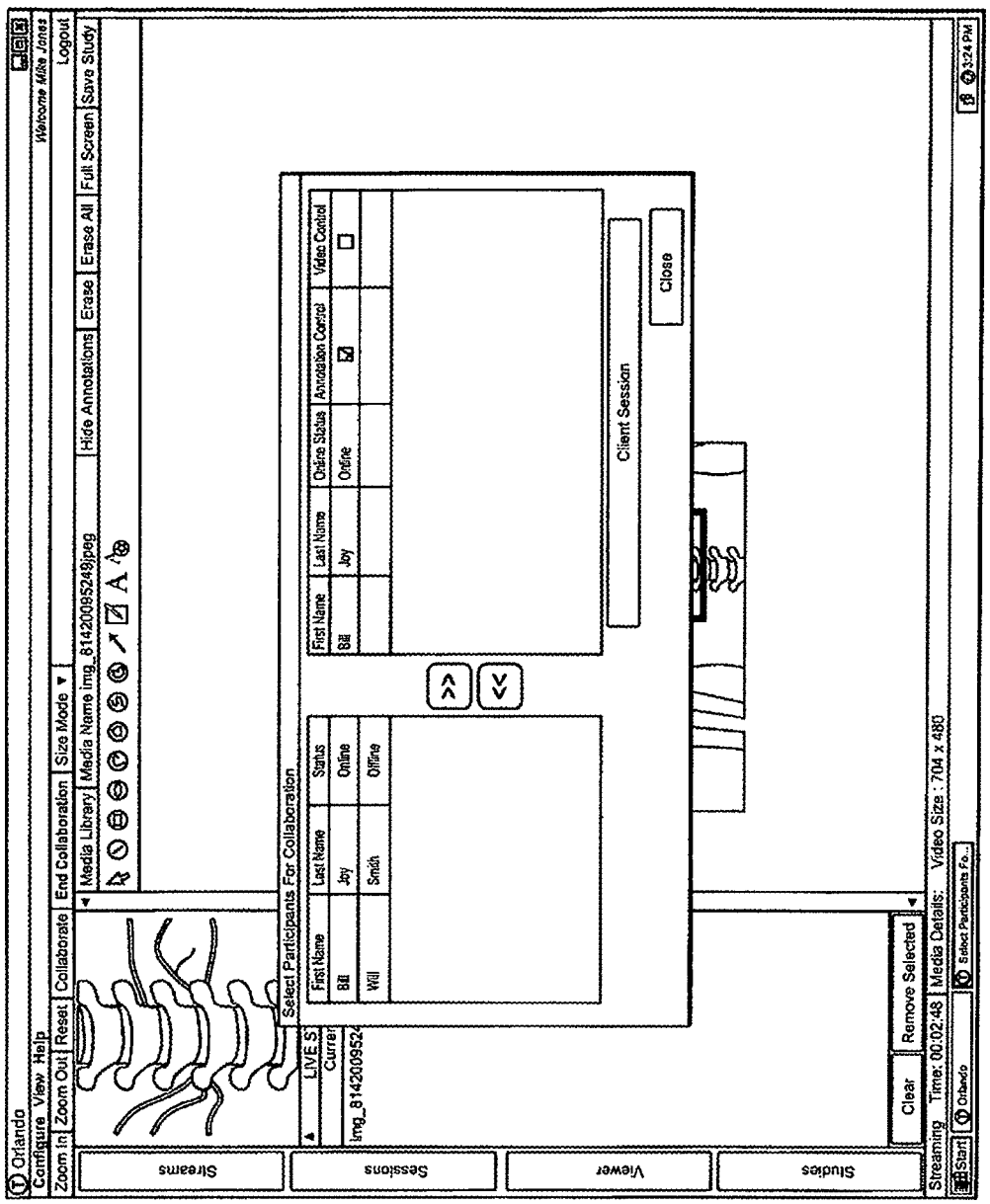

The TIMS Clini-Pod Clinical Network Server (CNS) 2 'single file encapsulate and save' functionality encapsulates and saves collaborated imagery files in a single file format structure, as may be required by standards for clinical documentation or medical records storage, including as specified in the DICOM Standard. Users can encapsulate and save collaborated imagery files in the Media Library on a computer storage device, as depicted in FIG. 4, which contain all of the input illustrations 18 from all participant clients 10. Users can also encapsulate and save collaborated imagery files on the TIMS Clini-Pod Clinical Network Server (CNS) 2, on a local storage device, on a PACS 4, or other DICOM compliant image repository, or on any other repository that requires streaming imagery data and metadata to be combined in a single file format structure, clinical data repositories, personalized clinical knowledge repositories, medical dicom vismeme vaults and metadata repositories.

Figure 9:
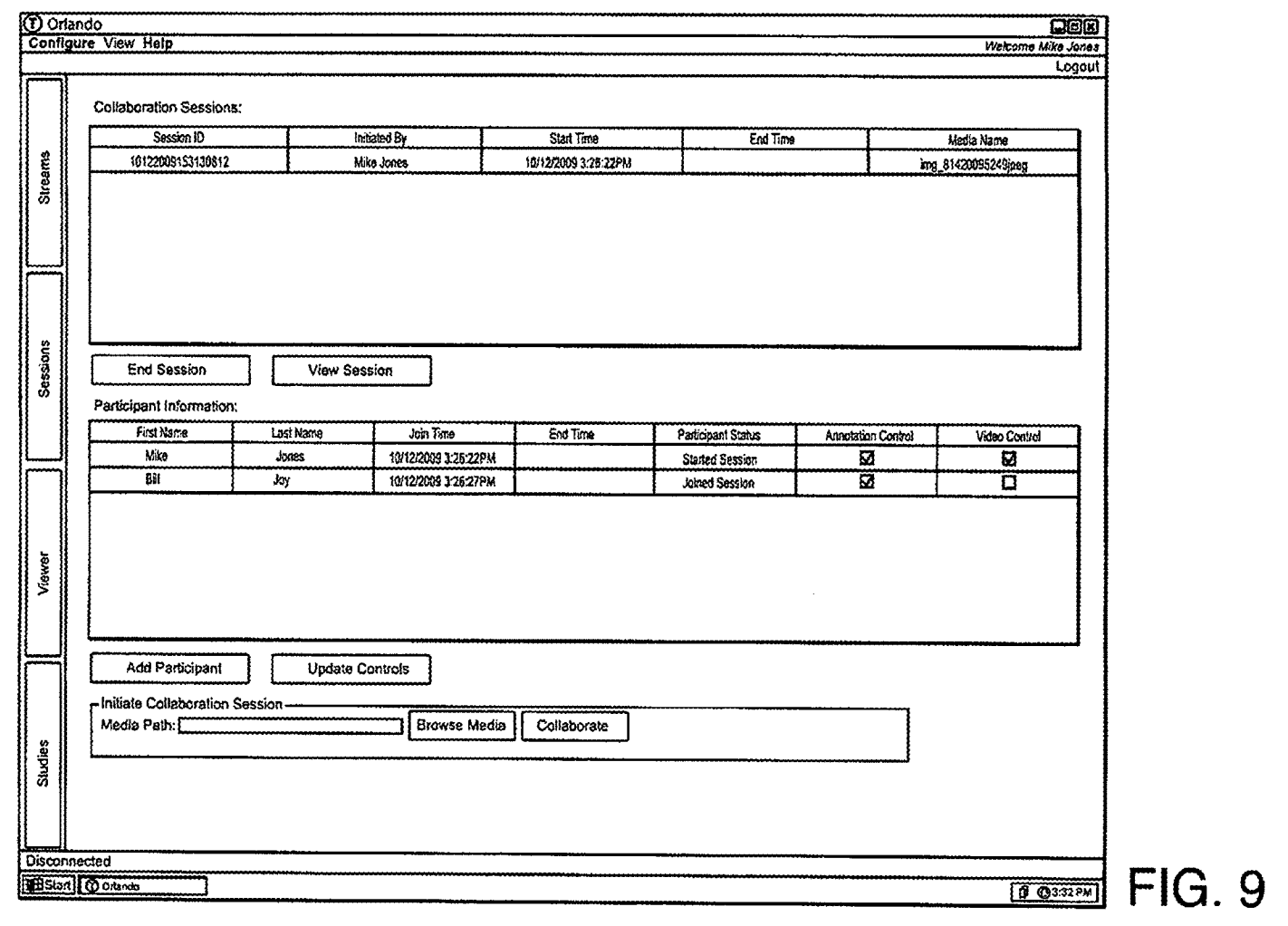

The TIMS Clini-Pod Clinical Network Server (CNS) 2 creates session logs that include collaboration session identification, participant client information, information about streaming imagery data, including associated patient metadata, along with session dates and times, as shown in FIG. 9.

In one embodiment, several participant clients 10, also known as Radiologist, Pathologist and Surgical Oncologist, utilize the network systems apparatus 1 to collaborate in the provision of oncology care. At Time 1, Radiologist retrieves patient's archived medical imagery from a PACS 4 image repository. Radiologist detects a suspicious nodule on several images and inputs telestrations 21 and drawings 22 indicating the location of the nodule, along with text annotations 23 charactering its clinical significance and voice annotations 23 summarizing his findings. The Radiologist utilizes the 'single file encapsulate and save' functionality of the network systems apparatus 1 to incorporate those input illustrations 18, together with medical imagery data 13 and identifying patient metadata, in a single file format structure, known as a collaborated imagery file (CIF #1). Radiologist archives the CIF #1, which has been encapsulated and saved in the DICOM Standard, to PACS 4 for review and discussion with other members of the oncology care team. At Time 2, Radiologist invites Pathologist to a collaboration session to discuss his findings of a suspicious nodule as described in CIF #1. While both participant clients 10 are concurrently viewing CIF #1, Radiologist retrieves several additional collaborated imagery files from the media library from PACS 4 of relevant prior patient medical imagery for display and viewing during the collaboration session, as shown in FIG. 4. Participant clients 10 record, encapsulate and save their input illustrations 18 for each of several imagery files selected for discussion during the collaboration session, as CIF #2, #3, #4. Pathologist combines CIF #1 with CIF #2, #3, #4 as collaborated imagery study (CIS #1) and stores CIS #1 on PACS 4 for subsequent review and discussion with Surgical Oncologist, who was unavailable at Time 2 to join collaboration session. At Time 3, Surgical Oncologist reviews CIS#1 and selects CIF #4 to create a surgical roadmap to guide tumor excision using input illustrations 18, which include telestrations 21, drawings 22, and voice annotations 23. Surgical Oncologist saves surgical roadmap as CIF #5. At Time 4, Surgical Oncologist retrieves surgical roadmap (CIF #5), for intra-operative guidance during tumor removal. At Time 5, during surgery, Surgical Oncologist invites Radiologist and Pathologist for intra-operative consultation during tumor excision. At Time 6, participant clients—Surgical Oncologist, Radiologist, and Pathologist—utilize network systems apparatus 1 to retrieve and concurrently view nodule (CIF #1), tumor pathology images (CIF #2, #3, #4), and surgical roadmap (CIF #5) from PACS 4, along with live streaming imagery data from endoscope 13 used during tumor excision.

Periodically during the surgical procedure, at Times 7,8,9, Surgical Oncologist consults with Pathologist to confirm sufficiency of margins around excised tumor. Pathologist confirms sufficiency of margins with telestrations 21, drawings 22, and text annotations 23, over live endoscopy images, saving all those input illustrations 18, together with associated streaming imagery data 13 in single file format structure as CIF #6. At Time 10, Surgical Oncologist retrieves CIF #6 from PACS 4, which contains Pathologist's input illustrations 18 regarding excised tumor margins, and dictates a post-operative surgical report adding voice annotations 23, to telestrations 21, and drawings 22 to endoscopic images from excision surgery and saving in single file format structure as CIF #7. At Time 11, Surgical Oncologist combines pre-operative surgical roadmap CIF #5 with post-operative surgical report CIF #7, along with pre-operative image study CIS #1 (which includes CIF #1, #2, #3, #4) into comprehensive clinical report (CIS #2) for distribution to the oncology care team.

Surgical Oncologist can encapsulate and save CIS #2 in a single file format structure as specified in the DICOM Standard and send to PACS 4. Surgical Oncologist utilizes the 'single file encapsulate and save' functionality of the network systems apparatus to encapsulate and save CIS #2 in a single file format structure as specified in the DICOM Standard and send to PACS 4. Surgical Oncologist can also encapsulate and save CIS #2 in single file format structure as may be required for clinical documents, for storage in patient's electronic medical record, or for patient billing. At Time 12, Surgical Oncologist retrieves CIS #2 from PACS 4, utilizes network systems apparatus 1 to remove all relevant identifying patient metadata, and encapsulates and saves as an anonymized collaborated imagery study (CIS #3) for use as teaching files with surgical fellows.

Figure 6:
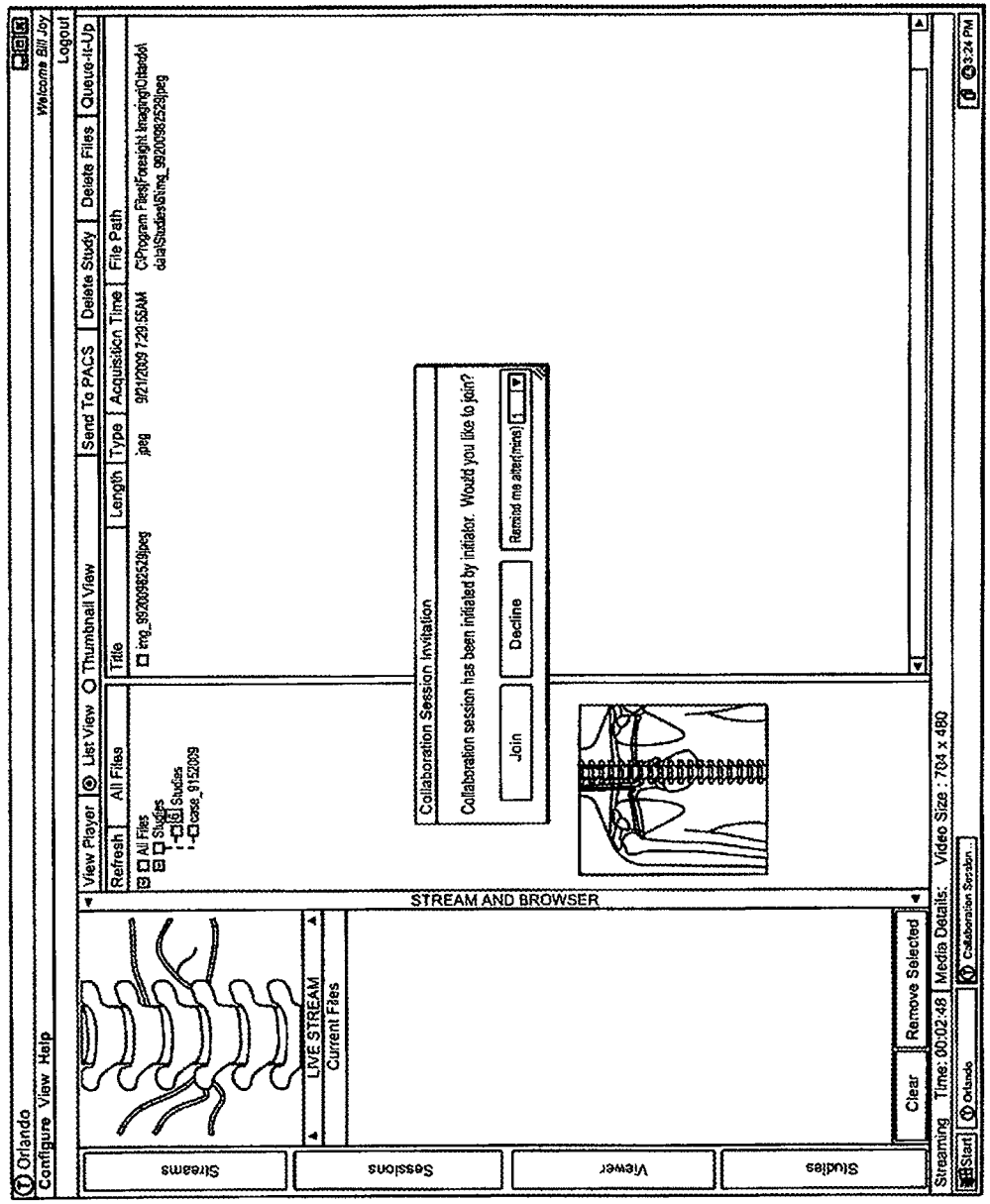
FIG. 6, shows a graphic user interface screen shot of collaboration initiated.
Figure 7:
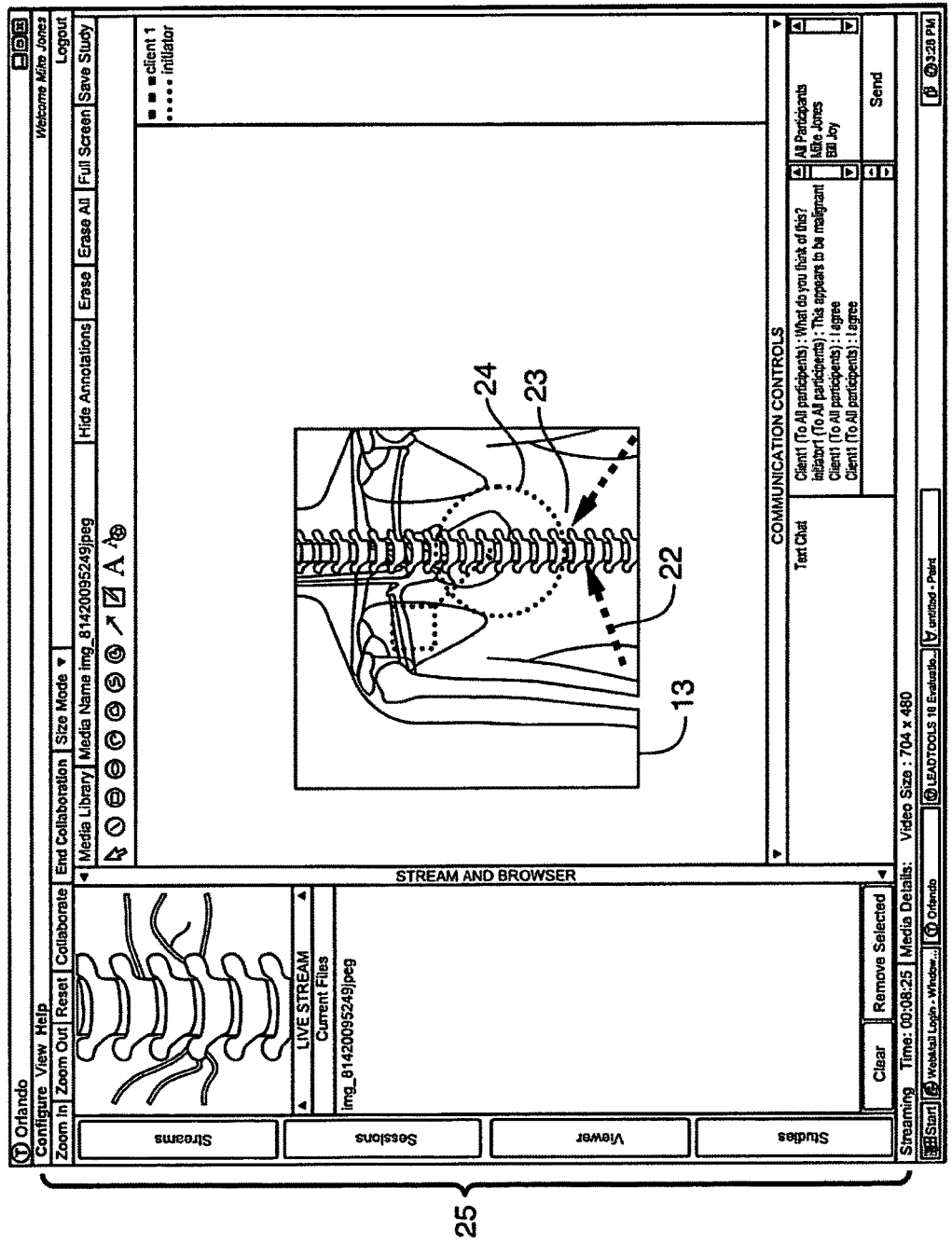
FIG. 7, shows a graphic user interface screen shot of collaboration session including medical image and illustrations.
Figure 8:
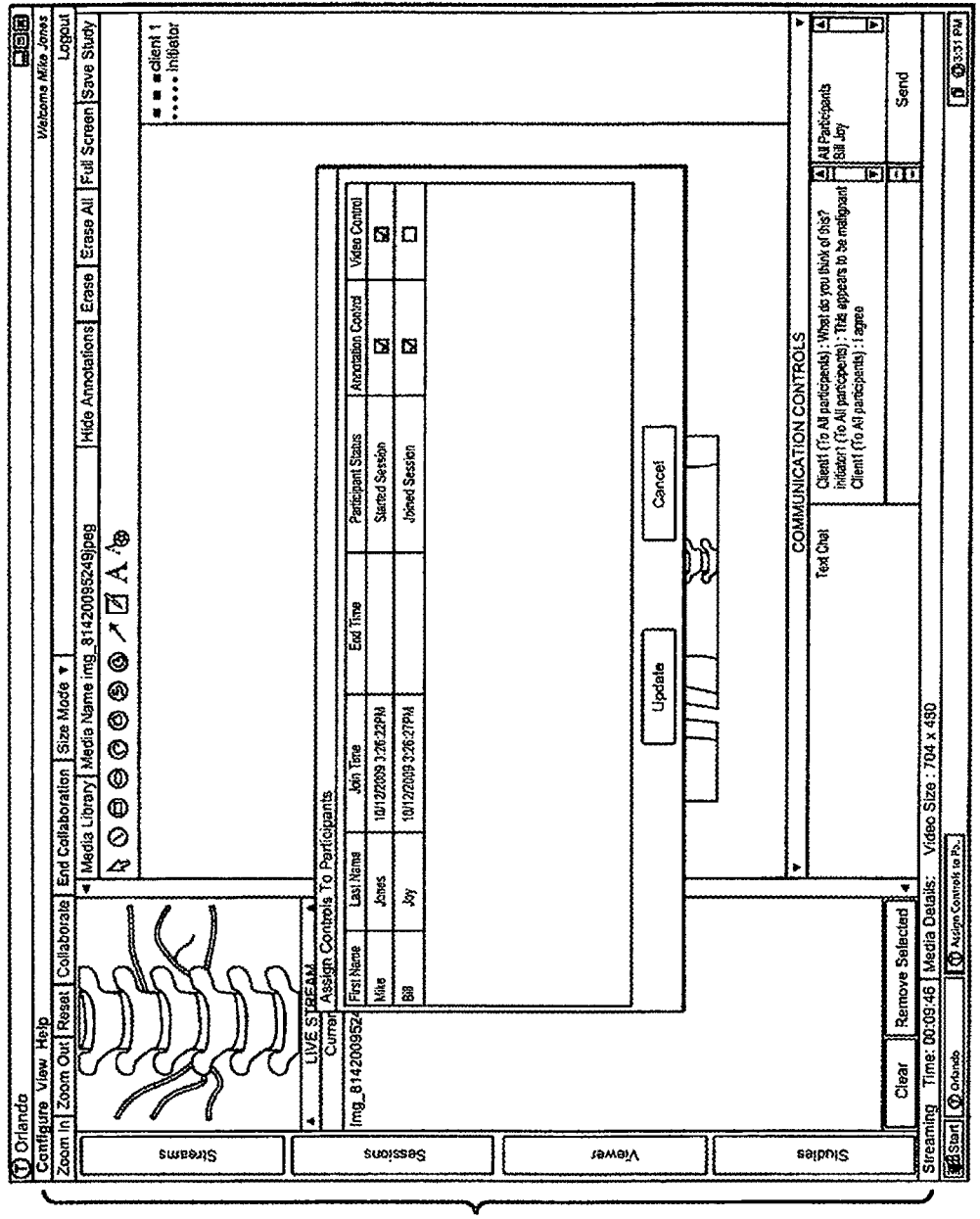
FIG. 8, shows a graphic user interface screen shot of client assignment of control to participants.
Figure 10:
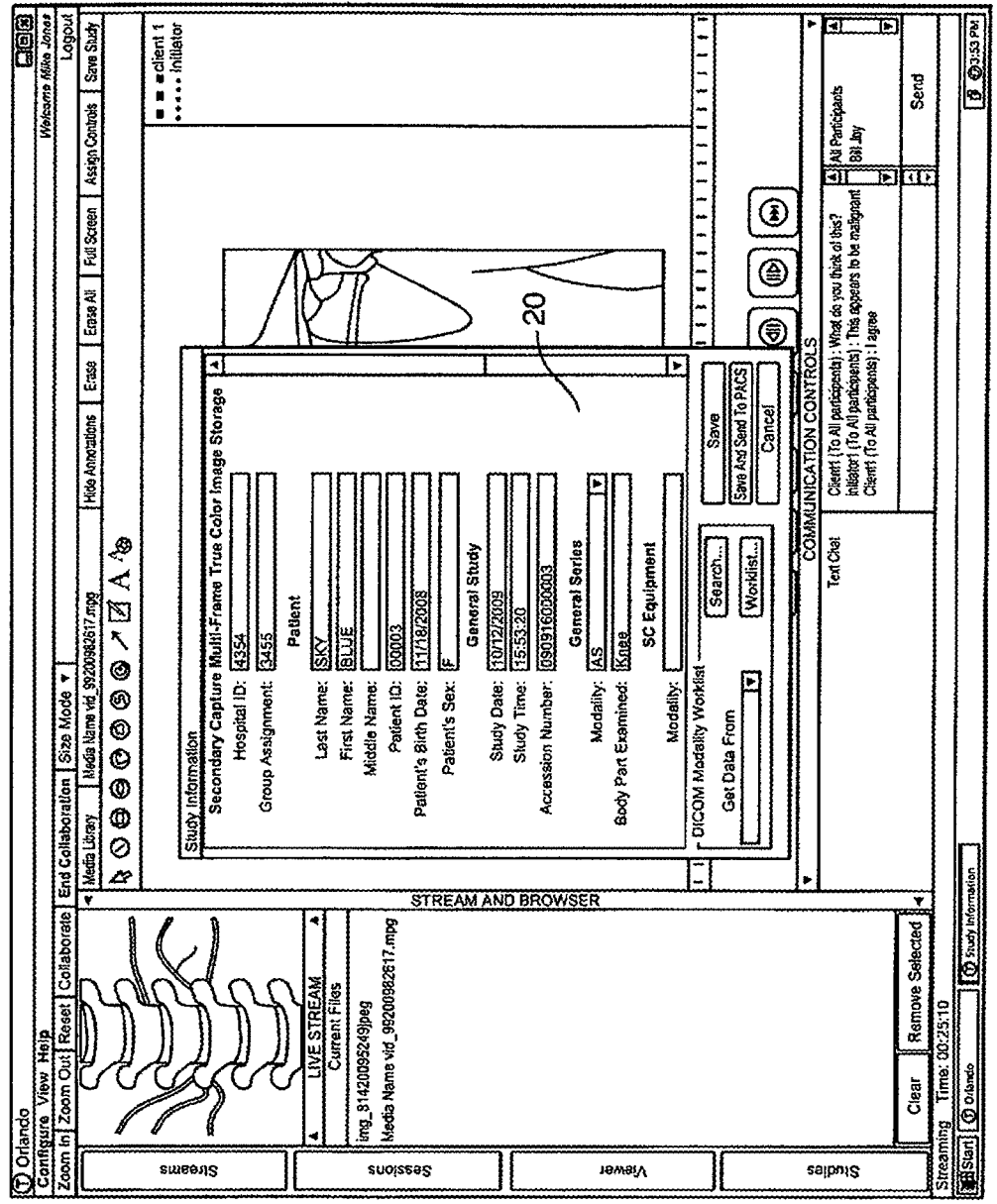
FIG. 10, shows a graphic user interface screen shot of patient image study information.
Figure 11:
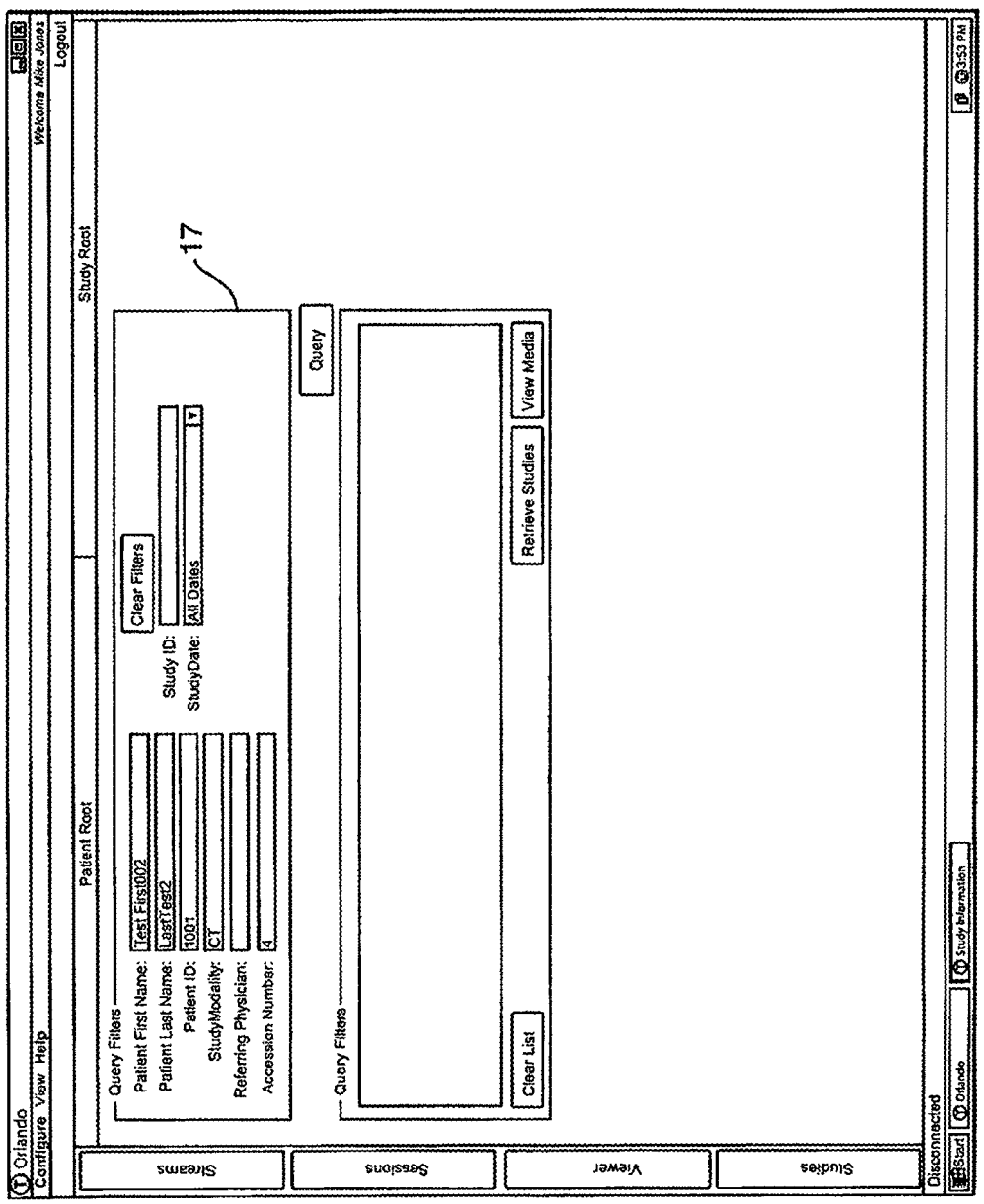
FIG. 11, shows a graphic user interface screen shot of patient database information.
Figure 12:
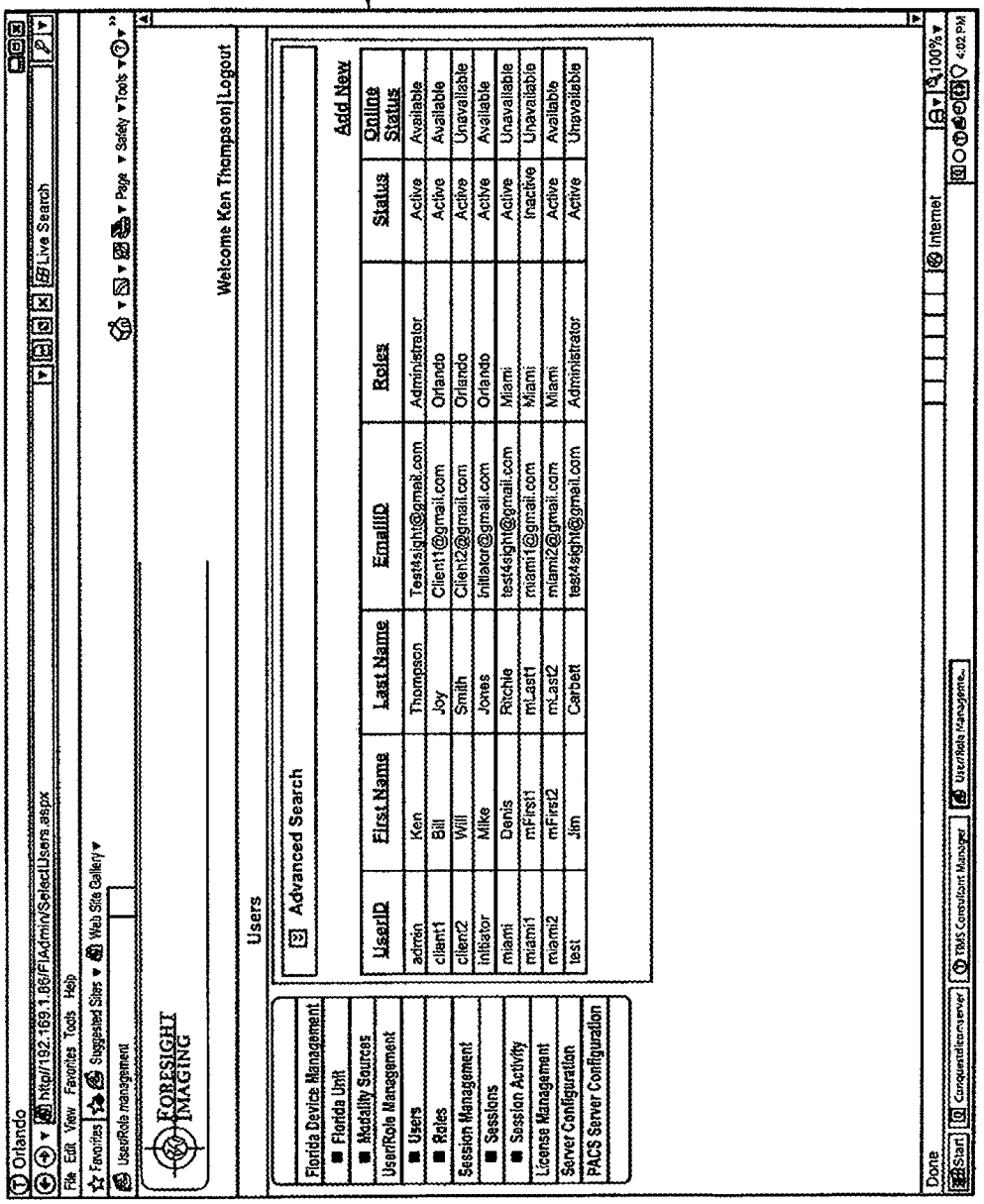
FIG. 12, shows a graphic user interface screen shot of administrative controls.
Figure 13:
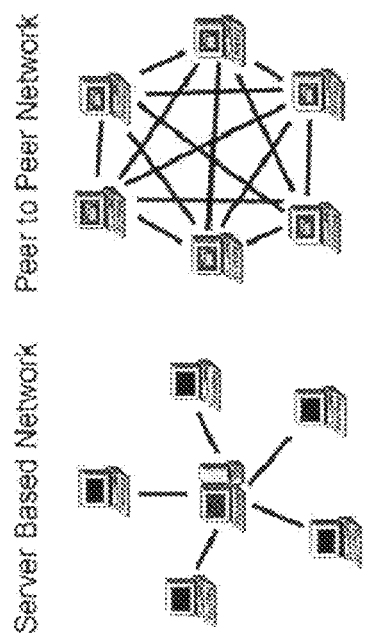
FIG. 13, shows a TIMS Clini-Pod deployment as hub- and spoke for either server-based or peer-to-peer networks.
Figure 13:
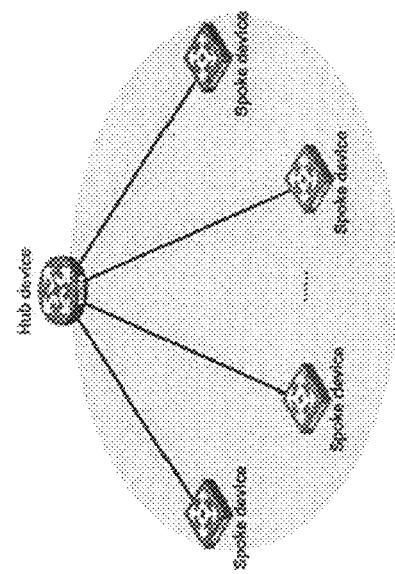
Figure 14:
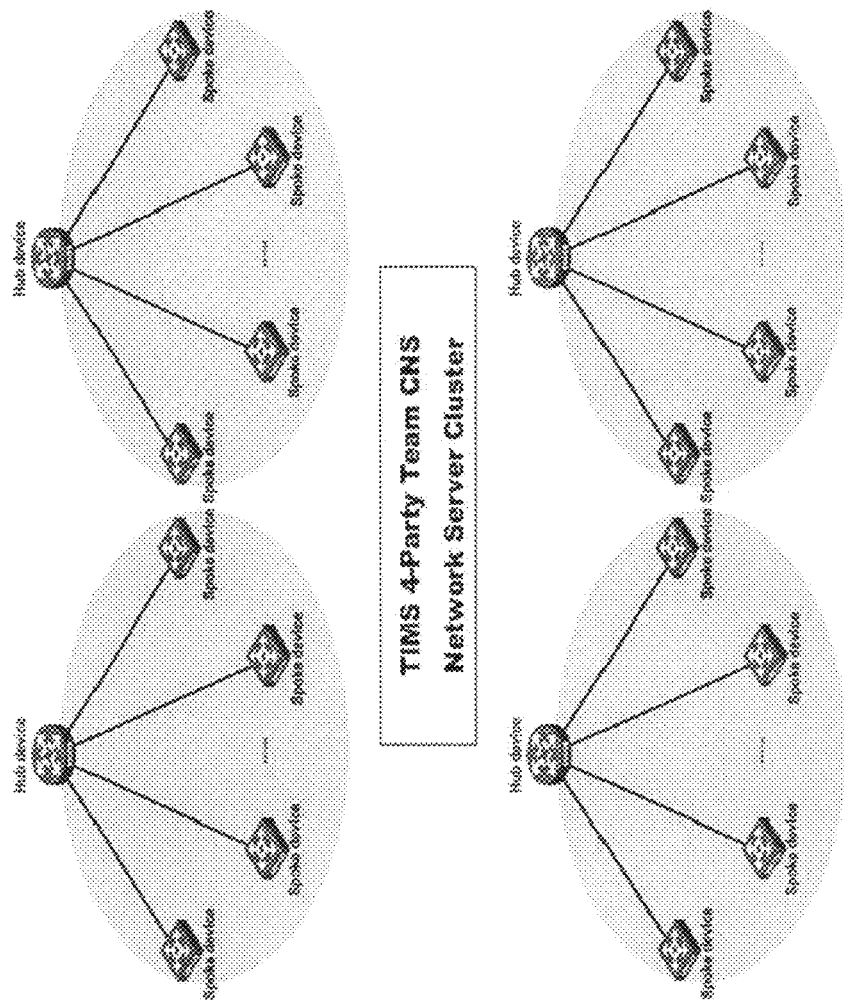
FIG. 14, shows a TIMS 4-Party Team CNS Network Server interconnecting with four TIMS Clini-Pods.
Figure 15:
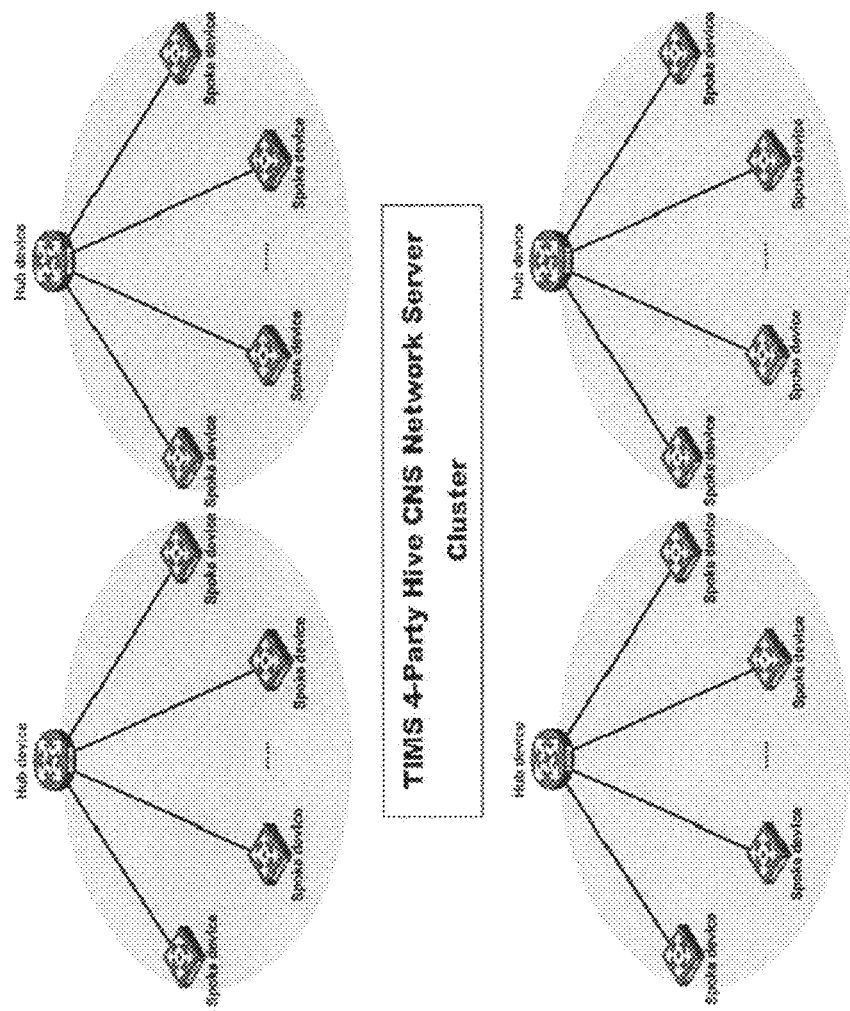
FIG. 15, shows a TIMS 4-Party Hive CNS Network Server interconnecting with four TIMS Team CNS Servers.
Figure 16:
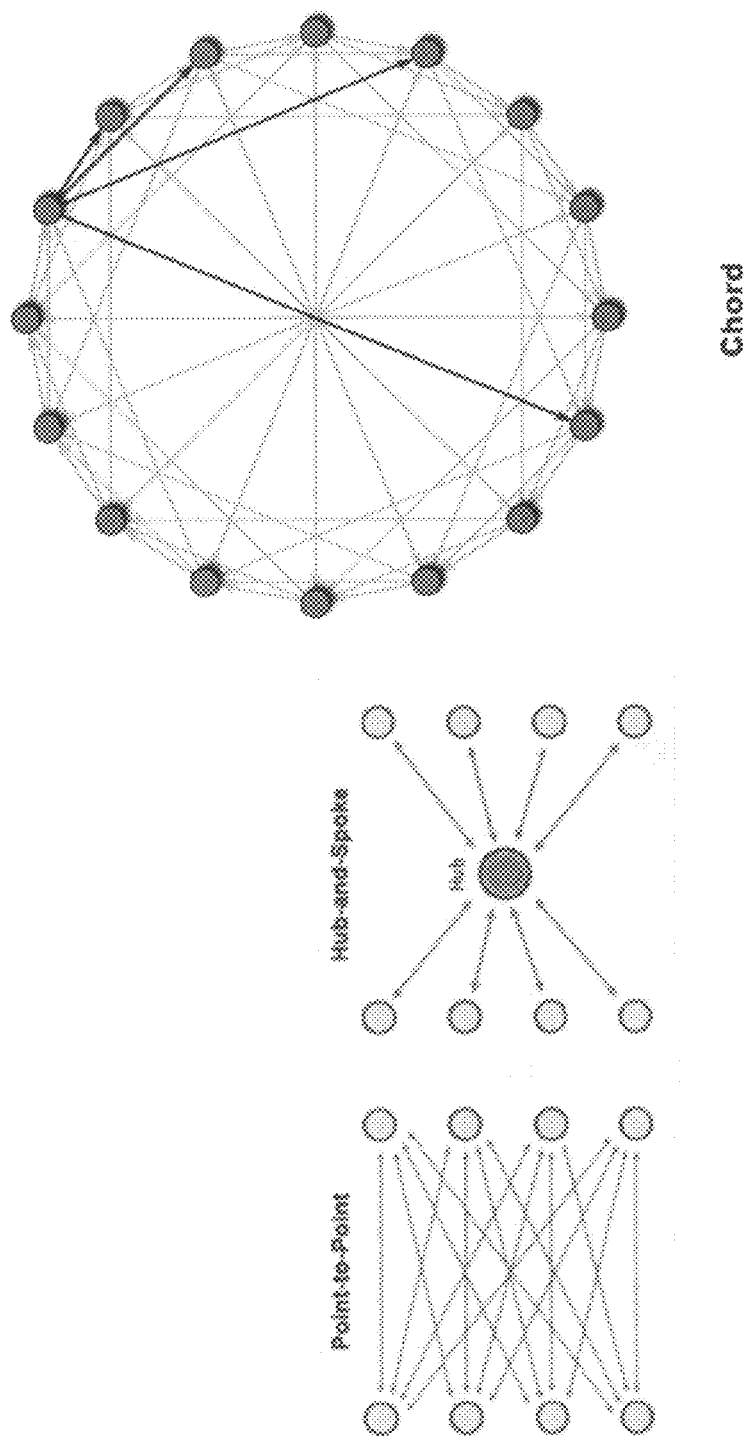
FIG. 16, shows Alternative Network Architecture Configurations for TIMS Clini-Pod Deployment: Point-to-Point vs Hub-and-Spoke vs Chord.

In another embodiment, a participant client 10, known as a Hospitalist, remotely monitors live streaming imagery data 13 from a surgical procedure in an operating room on channel one, and archived streaming imagery data 13 of a patient recovering in Intensive Care Unit, on channel two. While monitoring streaming imagery data 13 on channels one and two, as depicted in FIG. 3 and FIG. 7, Hospitalist accepts an invitation to join a collaboration session on channel three to monitor and consult live on a diagnostic procedure in the emergency room, as shown in FIG. 6. The live consultation involves review of patient images from an analog ultrasound machine and a digital CT scanner in the emergency room. During the collaboration session in the emergency room on channel three, Hospitalist utilizes the multi-channel viewing capability of Applicant's network systems apparatus 1 to continue live monitoring of streaming imagery data 13 on channel one and channel two, and to retrieve and view additional archived imagery data 13 of patient recovery in Intensive Care Unit.

In another embodiment, a patient is recalled to undergo a second PET/MRI scan. The previous test yielded inconclusive, due to patient motion during image capture, thus requiring a costly retest. During the second test, a Radiologist was able to review the MRI images captured 13 during the first portion of the test, while the patient was still being imaged in PET unit and confirm that the second MRI scan was useable. The Radiologist was able to advise the Attending Molecular Pathologist during PET scan 13 of additional regions of interest with input illustrations 18 for further investigation. In another embodiment, an Oncologist wishes to convene a virtual tumor board for the following day involving multi-specialist collaboration with a patient's Radiologist, Pathologist, Oncology Surgeon and himself. Oncologist sends invitations to colleagues along with several collaborated imagery files he wishes to review during the collaboration session. The Radiologist and pathologist confirm availability, but the Oncologist Surgeon is unable to attend. However, Oncology Surgeon is able to annotate 23 with telestrations 21 and drawings 22 on several key images 13 included in the collaborated imagery study sent with the session invitation. Oncology Surgeon also includes his clinical notes and an audio file along with his report, together all encapsulated as a CIF and returned to the session host.

During the collaboration session the following day, the host Oncologist retrieves patient images from PACS 4 and from his local media library 25 containing the CIF 13, 18 sent to him from the Oncology Surgeon, viewing both images concurrently when the radiology and pathology colleagues join the collaboration session. During the collaboration session, the Pathologist is monitoring on the third channel of the multi-channel streamer 7,8,9, 25, a tumor removal of another patient in the operating room, advising that Oncology Surgeon intra-operatively regarding sufficiency of margins of tumor removal from that patient. Oncology Surgeon is able to share live imagery 13 of the tumor removal with the radiology and oncology colleagues who have joined the virtual tumor board collaboration session.

At the conclusion of the collaboration session, the host Oncologist encapsulates and saves input illustrations 18 from participant clients 10, including encapsulated audio clinical notes and biopsy reports as clinical documents, saving them as collaborated imagery files and sending them to all participant clients 10 as well as invites unable to attend. Additionally, the CIFs 13, 18 are sent to PACS 4 for inclusion in the patient's electronic medical records as well to patient's referring clinician.

What is claimed is:

1. A network system allowing collaborator clients, to capture, retrieve and concurrently view at least one source of streaming medical modality imagery data, and one or more sources of heterogeneous streaming imagery data, medical and non-medical streaming imagery data, and combinations thereof including images, video, modality imagery, audio, video and haptic wave forms and files, genomic maps, multiomic-phenotypic, genomic, metabolomic-clinical data sets, biometric maps and movies, hapmaps, heat maps, data stream visualizations, structured reports, and clinical documents, both live and archived, for synchronous or asynchronous communications, collaboration, consultation and instruction with one or more collaborator clients, each collaborator client annotating over the heterogeneous streaming imagery data, comprising; a tele-visual imagery informatics management system including, at least one or more tele-visual imagery informatics management system, wherein each is a device adapted for independent acquisition and transmission of signals from other sources of streaming imagery data at native, enhanced or reduced resolutions, and native enhanced or reduced frame rates, used for the acquisition and transmission of, live or archived streaming imagery data, 1 including images, video, modality imagery, audio, video and haptic wave forms and files, genomic maps, multiomic-phenotypic, genomic, metabolomic-clinical data sets, biometric maps and movies, hapmaps, heat maps, data stream visualizations, structured reports, and clinical documents, analog or digital video signals in standard or non-standard resolutions, medical or non-medical imagery, in compressed or uncompressed imagery formats; at least one or more tele-visual imagery informatics management system clini-pod CNS network servers, a neurosynaptic network node comprising a streamer, splitter, router, server and storage device enabling at least one or more collaborants to concurrently view, communicate, collaborate, consult and instruct among collaborants using at least one or more sources of streaming imagery data acquired and transmitted by tele-visual imagery informatics management system clini-docks, including live streaming imagery data, archived streaming imagery data, appended streaming imagery metadata, collaborant annotations, and archived collaborated imagery files during a synchronous or asynchronous collaboration session; establishing and maintaining channel communications for each and all of the sources of streaming imagery data for at least one or more collaborants during a collaboration session, enabling at least one or more collaborants in at least one or more locations, to concurrently view, communicate, collaborate, consult and instruct among collaborants using at least one or more sources of live streaming imagery data, archived streaming imagery data, appended streaming imagery metadata, collaborant annotations, and archived collaborated imagery files from each collaborant during a collaboration session, 2 managing and controlling at least one or more associated databases, and privileges for authorization, authentication, identity management, security, access, publication and distribution for viewing, communicating, collaborating, consulting and instructing among collaborants managing and controlling privileges for at least one or more collaborants to encapsulate and save, store, retrieve and distribute live streaming imagery data, archived streaming imagery data, appended streaming imagery metadata, collaborant annotations, and archived collaborated imagery files for each collaborant during collaboration sessions; enabling both synchronous and asynchronous bidirectional communications with combinations of one or more local area networks, one or more wide area networks, including internet, and one or more streaming imagery data repositories during one or more collaboration sessions enabling identification, tracking and monitoring of collaborants by assignment of a unique color for annotations of streaming imagery data, archived collaborated imagery files and collaborant annotations, including telestrations, drawings, illustrations, alpha-numeric text notations, video annotations, voice annotations, haptic annotations and document annotations; and at least one or more tele-visual imagery informatics management system clini-ports allowing at least one or more collaborants, each, 3 capturing live streaming imagery data, capturing associated live streaming imagery metadata, retrieving archived streaming imagery data, retrieving archived associated imagery metadata, and transporting live streaming imagery data, transporting associated live streaming imagery metadata, and transporting live streaming imagery data, associated live streaming metadata, archived streaming imagery data, associated archived streaming metadata into collaboration sessions, concurrently view, communicate, collaborate, consult and instruct among collaborants using at least one or more sources of streaming imagery data, annotating streaming imagery data collaborant annotations, including telestrations, drawings, illustrations, alpha-numeric text notations, video annotations, voice annotations, haptic annotations and document annotations, and encapsulating streaming imagery data and associated streaming imagery metadata together with collaborant annotations in native, single file format structures, and saving said streaming imagery data and said associated streaming imagery metadata together with said collaborant annotations in at least one or more collaborated imagery files during collaboration sessions, including asynchronous or synchronous collaborations with at least one or more collaborants, communicate, collaborate, consult and instruct with one or more sources of streaming imagery data shared among one or more participant collaborants with a multi-channel stream viewer that enables capture, retrieval and concurrent viewing of both live and archived medical imagery streams together with associated metadata independently add sources of streaming imagery data, adjust, enhance or reduce resolutions or frame rates of streaming imagery data with a multi-channel communications control interface, and independently view those additional 4 channels of streaming imagery data and independently select which of those channels to bring into a collaboration session convey instructions with two way communications among collaborants, including source channel selection for imagery data streams with telestrations, drawings, illustrations, alpha-numeric text notations, image annotations, wave form annotations, voice annotations, video annotations, haptic annotations and document annotations and not reliant upon any external communications network.

2. The network system of claim 1 for the acquisition and transmission of heterogeneous sources of streaming imagery data, for synchronous or asynchronous communications, collaboration, consultation and instruction with one or more collaborator clients, each collaborator client annotating over the heterogeneous streaming imagery data, including medical video, medical modality imagery, medical wave form imagery, and clinical documents, and saving collaborated annotations together with streaming imagery data, relevant imagery metadata, including appended imagery metadata, from the collaboration session in native, single file format structures, known as collaborated imagery files;

storing collaborated imagery files from all participant collaborants locally in an image data repository on their respective computer storage devices, on image data repositories on the tele-visual imagery informatics management system servers, on a picture archiving and communications system repository, on other image data repositories compliant with standards for digital imaging and communications in medicine, or on any other data repository that requires streaming imagery data and metadata to be combined in native, single file format structures, including clinical data repositories, personalized knowledge repositories, vismemes vaults and metadata repositories retrieving collaborated imagery files from all participant collaborants stored locally in an data repository on their respective computer storage devices, on image data repositories on the tele-visual imagery informatics management system servers, on a picture archiving and communications system repository, on other image data repositories compliant with standards for digital imaging and communications in medicine, or on any other data repository that requires streaming imagery data and metadata to be combined in native, single file format structures, including clinical data repositories, personalized knowledge repositories, vismemes vaults and metadata repositories publishing and distributing collaborated imagery files in known native, single file format structures, including those used for digital imaging and communications in medicine comprising both core and non-core data element tags, together with conformance statements that enable prior evaluation and testing of streaming imagery equipment components without an actual physical connection, all of which facilitate network connectivity for imagery equipment components, communication interoperability for imagery data systems, and exchange of collaborated imagery files.

3. The network system of claim 1 for the acquisition and transmission of medical streaming imagery data, including medical images, medical video, medical modality imagery, medical wave form imagery, clinical maps, genomic maps, multiomic-phenotypic, genomic, metabolomic-clinical data sets, biometric maps and movies, hapmaps, heat maps, data stream visualizations, clinical structured reports, and clinical documents, the network system preserving the clinical integrity of medical streaming imagery data from medical devices, systems and equipment cleared for medical use, including clinical diagnostic purposes, care delivery and patient monitoring, during synchronous or asynchronous communications, collaboration, consultation, instruction, curation, annotation and tagging of streaming medical imagery data, including recursive cognitive enrichments thereof, for use with medical devices, equipment, systems, image and data repositories, in native, single file format structures, including those compliant with standards for digital imaging and communications in medicine.

4. The network system of claim 1 for communications, collaboration, consultation and instruction in collaborator sessions among participant collaborants, collaborated imagery files created from collaborant annotations, session metadata and medical streaming imagery data, including data cleared for clinical diagnostic purposes, that can be encapsulated and saved together as collaborated medical imagery files and cleared for use with approved medical devices, equipment, systems, image and data repositories, in native, single file format structures, including those compliant with standards for digital imaging and communications in medicine.

5. The network system of claim 1 for archived collaborated imagery files that can be retrieved for use together with streaming imagery data during synchronous or asynchronous collaboration sessions, revised, appended, annotated, encapsulated and saved in native, single file format structures, including those compliant with standards for digital imaging and communications in medicine, during a collaboration session, and made available for use together with streaming imagery data during current or subsequent collaboration sessions.

6. A method allowing collaborator clients, to capture, retrieve and concurrently view at least one source of streaming medical modality imagery data, and one or more sources of heterogeneous streaming imagery data, medical and non-medical streaming imagery data, and combinations thereof including images, video, modality imagery, audio, video and haptic wave forms and files, genomic maps, multiomic-phenotypic, genomic, metabolomic-clinical data sets, biometric maps and movies, hapmaps, heat maps, data stream visualizations, structured reports, and clinical documents, both live and archived, for synchronous or asynchronous communications, collaboration, consultation and instruction with one or more collaborator clients, each collaborator client annotating over the heterogeneous streaming imagery data, comprising;

a tele-visual imagery informatics management system consisting of the following essential components:

one or more tele-visual imagery informatics management system clini-docks;
each of which is a device adapted for independent acquisition and transmission of signals from other sources of streaming imagery data at native, enhanced or reduced resolutions and native, enhanced or reduced frame rates, used for the acquisition and transmission of, live or archived streaming imagery data, including images, video, modality imagery, audio, video and haptic wave forms and files, genomic maps, multiomic-phenotypic, genomic, metabolomic-clinical data sets, biometric maps and movies, hapmaps, heat maps, data stream visualizations, structured reports, and clinical documents, analog or digital video signals in standard or non-standard resolutions, medical or non-medical imagery, in compressed or uncompressed imagery formats,
one or more tele-visual imagery informatics management system clini-pod CNS network servers, a neurosynaptic network node comprising a streamer, splitter, router, server and storage device that;
enables concurrent collaboration with each and all of the one or more sources of streaming imagery data acquired and transmitted by tele-visual imagery informatics management system clini-docks,
establishes and maintains channel communications for each and all of the one or more sources of streaming imagery data each collaborator client wishes to view, monitor and collaborate with,
enables one or more collaborator clients to concurrently view, communicate, collaborate, consult and instruct with live streaming imagery data, archived imagery data, appended imagery metadata, collaborated annotations, and archived collaborated imagery files during a synchronous or asynchronous collaboration session,
enables one or more collaborator clients in multiple locations, some of whom may be located remotely to the sources of streaming imagery data, to concurrently view, communicate, collaborate, consult and instruct with live streaming imagery data, archived imagery data, appended imagery metadata, collaborated annotations, and archived collaborated imagery files from each collaborator client during the collaboration session,
dynamically manages and controls with one or more associated databases, authorization, authentication, identity management, security, and access, publication and distribution privileges for viewing, communicating, collaborating, consulting and instructing, and collaborant privileges for encapsulation and saving, storage, retrieval and distribution of live streaming imagery data, archived imagery data, appended imagery metadata, collaborated annotations, and archived collaborated imagery files for each collaborator client during collaboration sessions;
enables both synchronous and asynchronous bidirectional communications with one or more local area networks, one or more wide area networks (internet) including imagery data repositories and combinations thereof during multiple collaboration sessions
enables identification, tracking and monitoring of collaborants by assignment of a unique color for annotations of streaming imagery data, archived collaborated imagery files and collaborant annotations, that include telestrations, drawings, illustrations, alpha-numeric text notations, as well as collaborant annotations combined with video annotations, voice annotations, haptic annotations and document annotations
one or more tele-visual imagery informatics management system clini-ports that allows for multiple collaborants, each of whom can
capture live streaming imagery data together with associated imagery metadata and bring into the collaboration session,
retrieve archived streaming imagery data together with associated imagery metadata and bring into the collaboration session,
concurrently view, communicate, collaborate, consult and instruct with streaming imagery data,
annotate that streaming imagery data with collaborated annotations that include telestrations, drawings, illustrations, alpha-numeric text notations, image annotations, wave form annotations, voice annotations, video annotations, haptic annotations and document annotations,
encapsulate and save collaborated streaming imagery data and archived imagery metadata together with appended imagery metadata and collaborated annotations and from each collaboration session, including asynchronous or synchronous collaboration with one or more collaborants, in native, single file format structures, known as collaborated imagery files,
communicate, collaborate, consult and instruct with one or more sources of streaming imagery data shared among one or more participant collaborants with a multi-channel stream viewer that enables capture, retrieval and concurrent viewing of both live and archived medical imagery streams together with associated metadata
independently add sources of streaming imagery data, adjust, enhance or reduce resolutions or frame rates of streaming imagery data with a multi-channel communications control interface, and independently view those additional channels of streaming imagery data and independently select which of those channels to bring into a collaboration session
convey instructions with two way communications among collaborants, including source channel selection for imagery data streams with telestrations, drawings, illustrations, alpha-numeric text notations, image annotations, wave form annotations, voice annotations, video annotations, haptic annotations and document annotations and not reliant upon any external communications network.

7. The method of claim 6 for the acquisition and transmission of heterogeneous sources of streaming imagery data, for synchronous or asynchronous communications, collaboration, consultation and instruction with one or more collaborator clients, each collaborator client annotating over the heterogeneous streaming imagery data, including medical video, medical modality imagery, medical wave form imagery, and clinical documents, and saving collaborated annotations together with streaming imagery data, relevant imagery metadata, including appended imagery metadata, from the collaboration session in native, single file format structures, known as collaborated imagery files;
storing collaborated imagery files from all participant collaborators locally in an image data repository on their respective computer storage devices, on image data repositories on the tele-visual imagery informatics management system servers, on a picture archiving and communications system repository, on other image data repositories compliant with standards for digital imaging and communications in medicine, or on any other data repository that requires streaming imagery data and metadata to be combined in native, single file format structures, including clinical data repositories, personalized knowledge repositories, vismemes vaults and metadata repositories retrieving collaborated imagery files from all participant collaborants stored locally in an data repository on their respective computer storage devices, on image data repositories on the tele-visual imagery informatics management system servers, on a picture archiving and communications system repository, on other image data repositories compliant with standards for digital imaging and communications in medicine, or on any other data repository that requires streaming imagery data and metadata to be combined in native, single file format structures, including clinical data repositories, personalized knowledge repositories, vismemes vaults and metadata repositories publishing and distributing collaborated imagery files in known native, single file format structures, including those used for digital imaging and communications in medicine comprising both core and non-core data element tags, together with conformance statements that enable prior evaluation and testing of streaming imagery equipment components without an actual physical connection, all of which facilitate network connectivity for imagery equipment components, communication interoperability for imagery data systems, and exchange of collaborated imagery files.

8. The method of claim 6 for the acquisition and transmission of medical streaming imagery data, including medical images, medical video, medical modality imagery, medical wave form imagery, clinical maps, genomic maps, multiomic-phenotypic, genomic, metabolomic-clinical data sets, biometric maps and movies, hapmaps, heat maps, data stream visualizations, clinical structured reports, and clinical documents, the method preserving the clinical integrity of medical streaming imagery data from medical devices systems and equipment cleared for medical use, including clinical diagnostic purposes, care delivery and patient monitoring, during synchronous or asynchronous communications, collaboration, consultation, instruction, curation, annotation and tagging of streaming medical imagery data, including recursive cognitive enrichments thereof, for use with medical devices, equipment, systems, image and data repositories, in native, single file format structures, including those compliant with standards for digital imaging and communications in medicine.

9. The method of claim 6 for communications, collaboration, consultation and instruction in collaborator sessions among participant collaborants, collaborated imagery files created from collaborant annotations, session metadata and medical streaming imagery data, including data cleared for clinical diagnostic purposes, that can be encapsulated and saved together as collaborated medical imagery files and cleared for use with approved medical devices, equipment, systems, image and data repositories, including those compliant with standards for digital imaging and communications in medicine.

10. The method of claim 6 for archived collaborated imagery files that can be retrieved for use together with streaming imagery data during synchronous or asynchronous collaboration sessions, revised, appended, annotated, encapsulated and saved in native, single file format structures, including those compliant with standards for digital imaging and communications in medicine, during a collaboration session, and made available for use together with streaming imagery data during current or subsequent collaboration sessions.

11. The method of claim 6 for recursive cognitive enrichment and collaborative knowledge exchange with neurosynaptic network communications among collaborants, with one or more sources of multichannel, multiplexed heterogeneous streaming imagery data, including both medical and non-medical streaming imagery data, and combinations thereof, and together with images, video, modality imagery, waveforms, audio and haptic files, genomic maps, multiomic-phenotypic, genomic, metabolomic-clinical data sets, biometric maps and movies, hapmaps, heat maps, data stream visualizations, structured reports, and clinical documents.

12. The method of claim 6 for rapid, adaptive deep learning and multisensory skills acquisition with neurosynaptic network communications among collaborants, with one or more sources of multichannel, multiplexed heterogeneous streaming imagery data, including both medical and non-medical streaming imagery data, and combinations thereof, and together with images, video, modality imagery, waveforms, audio and haptic files, genomic maps, multiomic-phenotypic, genomic, metabolomic-clinical data sets, biometric maps and movies, hapmaps, heat maps, data stream visualizations, structured reports, and clinical documents.

13. The method of claim 6 for iterative cognitive design and collaborative value exchange with neurosynaptic network communications among collaborants, with one or more sources of multichannel, multiplexed heterogeneous streaming imagery data, including both medical and non-medical streaming imagery data, and combinations thereof, and together with images, video, modality imagery, waveforms, audio and haptic files, genomic maps, multiomic-phenotypic, genomic, metabolomic-clinical data sets, biometric maps and movies, hapmaps, heat maps, data stream visualizations, structured reports, and clinical documents.

* * * * *